(12) United States Patent  (10) Patent No.: US 8,286,876 B2
Mullen et al.                (45) Date of Patent:      Oct. 16, 2012

(54) CARDS AND DEVICES WITH MAGNETIC EMULATORS AND MAGNETIC READER READ-HEAD DETECTORS

(75) Inventors: Jeffrey D. Mullen, Pittsburgh, PA (US); David Lambeth, Pittsburgh, PA (US); Bruce Cloutier, Jeannette, PA (US)

(73) Assignee: Dynamics Inc., Pittsburgh, PA (US)

( * ) Notice: Subject to any disclaimer, the term of this patent is extended or adjusted under 35 U.S.C. 154(b) by 0 days.

(21) Appl. No.: 13/186,507

(22) Filed: Jul. 20, 2011

(65) Prior Publication Data

US 2011/0272465 A1    Nov. 10, 2011

Related U.S. Application Data

(63) Continuation of application No. 12/339,046, filed on Dec. 19, 2008.

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.
*G06K 7/08*     (2006.01)
*G06K 5/00*     (2006.01)
*G06K 19/00*    (2006.01)
*G06K 19/06*    (2006.01)
*G07F 19/00*    (2006.01)
*G07D 11/00*    (2006.01)
*G06Q 40/00*    (2012.01)

(52) U.S. Cl. ........ 235/449; 235/379; 235/487; 235/492; 235/493; 235/380

(58) Field of Classification Search .................. 235/449, 235/375, 379, 487, 492, 493
See application file for complete search history.

(56) References Cited

U.S. PATENT DOCUMENTS

| | | | | |
|---|---|---|---|---|
| 3,731,085 | A | * | 5/1973 | Bostrom ...................... 235/449 |
| 4,114,032 | A | * | 9/1978 | Brosow et al. ............... 235/493 |
| 4,296,315 | A | * | 10/1981 | Weimer et al. .............. 235/460 |
| 4,353,064 | A | | 10/1982 | Stamm |

(Continued)

FOREIGN PATENT DOCUMENTS

EP         0203683        12/1986

(Continued)

OTHER PUBLICATIONS

U.S. Appl. No. 60/594,300, filed Mar. 1, 2004, Poidomani et al.

(Continued)

*Primary Examiner* — Daniel Walsh

(57) ABSTRACT

A payment card (e.g., credit and/or debit card) is provided with a magnetic emulator operable to act as a magnetic stripe read-head detector and a data transmitter. A multiple layer flexible PCB may be fabricated to include multiple magnetic emulators. Layers of the flexible PCB may include magnetic shielding in order to reduce interference from the magnetic emulators to particular read-heads on a magnetic stripe reader.

16 Claims, 20 Drawing Sheets

U.S. PATENT DOCUMENTS

| | | | |
|---|---|---|---|
| 4,394,654 A | 7/1983 | Hofmann-Cerfontaine | |
| 4,614,861 A | 9/1986 | Pavlov et al. | |
| 4,667,087 A | 5/1987 | Quintana | |
| 4,701,601 A | 10/1987 | Francini et al. | |
| 4,720,860 A | 1/1988 | Weiss | |
| 4,786,791 A | 11/1988 | Hodama | |
| 4,789,776 A | 12/1988 | Inoue | |
| 4,791,283 A * | 12/1988 | Burkhardt | 235/438 |
| 4,797,542 A | 1/1989 | Hara | |
| 4,849,616 A | 7/1989 | Mizote | |
| 4,902,146 A | 2/1990 | Ishikawa | |
| 4,977,040 A * | 12/1990 | Yano et al. | 428/839.1 |
| 5,038,251 A | 8/1991 | Sugiyama et al. | |
| RE34,096 E * | 10/1992 | Golightly | 235/380 |
| 5,168,520 A | 12/1992 | Weiss | |
| 5,237,614 A | 8/1993 | Weiss | |
| 5,254,843 A | 10/1993 | Hynes et al. | |
| 5,276,311 A | 1/1994 | Hennige | |
| 5,321,817 A | 6/1994 | Feinstein | |
| 5,347,580 A | 9/1994 | Molva et al. | |
| 5,361,062 A | 11/1994 | Weiss et al. | |
| 5,412,199 A | 5/1995 | Finkelstein et al. | |
| 5,434,398 A | 7/1995 | Goldberg | |
| 5,434,405 A | 7/1995 | Finkelstein et al. | |
| 5,477,038 A | 12/1995 | Levine et al. | |
| 5,478,994 A | 12/1995 | Rahman | |
| 5,479,512 A | 12/1995 | Weiss | |
| 5,484,997 A | 1/1996 | Haynes | |
| 5,485,519 A | 1/1996 | Weiss | |
| 5,585,787 A * | 12/1996 | Wallerstein | 340/5.42 |
| 5,591,949 A | 1/1997 | Bernstein | |
| 5,608,203 A | 3/1997 | Finkelstein et al. | |
| 5,623,552 A | 4/1997 | Lane | |
| 5,657,388 A | 8/1997 | Weiss | |
| 5,748,737 A | 5/1998 | Daggar | |
| 5,834,747 A | 11/1998 | Cooper | |
| 5,834,756 A | 11/1998 | Gutman et al. | |
| 5,844,230 A | 12/1998 | Lalonde | |
| 5,856,661 A | 1/1999 | Finkelstein et al. | |
| 5,864,623 A | 1/1999 | Messina et al. | |
| 5,883,377 A | 3/1999 | Chapin, Jr. | |
| 5,886,874 A | 3/1999 | Onoda et al. | |
| 5,907,142 A | 5/1999 | Kelsey | |
| 5,913,203 A | 6/1999 | Wong et al. | |
| 5,937,394 A | 8/1999 | Wong et al. | |
| 5,941,375 A * | 8/1999 | Kamens et al. | 206/38 |
| 5,955,021 A | 9/1999 | Tiffany, III | |
| 5,955,961 A * | 9/1999 | Wallerstein | 340/5.4 |
| 5,956,699 A | 9/1999 | Wong et al. | |
| 6,012,636 A | 1/2000 | Smith | |
| 6,025,054 A | 2/2000 | Tiffany, III | |
| 6,045,043 A | 4/2000 | Bashan et al. | |
| 6,076,163 A | 6/2000 | Hoffstein et al. | |
| 6,085,320 A | 7/2000 | Kaliski | |
| 6,095,416 A | 8/2000 | Grant et al. | |
| 6,129,277 A | 10/2000 | Grant et al. | |
| 6,130,621 A | 10/2000 | Weiss | |
| 6,145,079 A | 11/2000 | Mitty et al. | |
| 6,157,920 A | 12/2000 | Jakobsson et al. | |
| 6,161,181 A | 12/2000 | Haynes, III et al. | |
| 6,176,430 B1 | 1/2001 | Finkelstein et al. | |
| 6,177,176 B1 * | 1/2001 | Tanabe et al. | 428/192 |
| 6,182,894 B1 | 2/2001 | Hackett et al. | |
| 6,189,098 B1 | 2/2001 | Kaliski | |
| 6,199,052 B1 | 3/2001 | Mitty et al. | |
| 6,206,293 B1 | 3/2001 | Gutman et al. | |
| 6,240,184 B1 | 5/2001 | Huynh et al. | |
| 6,241,153 B1 | 6/2001 | Tiffany, III | |
| 6,256,873 B1 | 7/2001 | Tiffany, III | |
| 6,269,163 B1 | 7/2001 | Rivest et al. | |
| 6,286,022 B1 | 9/2001 | Kaliski et al. | |
| 6,308,890 B1 | 10/2001 | Cooper | |
| 6,313,724 B1 | 11/2001 | Osterweil | |
| 6,389,442 B1 | 5/2002 | Yin et al. | |
| 6,393,447 B1 | 5/2002 | Jakobsson et al. | |
| 6,398,115 B2 | 6/2002 | Krause | |
| 6,402,029 B1 | 6/2002 | Gangi | |
| 6,411,715 B1 | 6/2002 | Liskov et al. | |
| 6,446,052 B1 | 9/2002 | Juels | |
| 6,460,141 B1 | 10/2002 | Olden | |
| 6,592,044 B1 | 7/2003 | Wong et al. | |
| 6,607,127 B2 | 8/2003 | Wong | |
| 6,609,654 B1 | 8/2003 | Anderson et al. | |
| 6,631,849 B2 | 10/2003 | Blossom | |
| 6,655,585 B2 | 12/2003 | Shinn | |
| 6,681,988 B2 | 1/2004 | Stack et al. | |
| 6,705,520 B1 | 3/2004 | Pitroda et al. | |
| 6,755,341 B1 | 6/2004 | Wong et al. | |
| 6,764,005 B2 | 7/2004 | Cooper | |
| 6,769,618 B1 | 8/2004 | Finkelstein | |
| 6,805,288 B2 | 10/2004 | Routhenstein et al. | |
| 6,811,082 B2 | 11/2004 | Wong | |
| 6,813,354 B1 | 11/2004 | Jakobsson et al. | |
| 6,817,532 B2 | 11/2004 | Finkelstein | |
| 6,873,974 B1 | 3/2005 | Schutzer | |
| 6,902,116 B2 | 6/2005 | Finkelstein | |
| 6,970,070 B2 | 11/2005 | Juels et al. | |
| 6,980,969 B1 | 12/2005 | Tuchler et al. | |
| 6,985,583 B1 | 1/2006 | Brainard et al. | |
| 6,991,155 B2 | 1/2006 | Burchette, Jr. | |
| 7,013,030 B2 | 3/2006 | Wong et al. | |
| 7,035,443 B2 | 4/2006 | Wong | |
| 7,039,223 B2 | 5/2006 | Wong | |
| 7,044,394 B2 | 5/2006 | Brown | |
| 7,051,929 B2 | 5/2006 | Li | |
| 7,073,721 B2 * | 7/2006 | Kano et al. | 235/488 |
| 7,083,094 B2 | 8/2006 | Cooper | |
| 7,097,108 B2 * | 8/2006 | Zellner et al. | 235/492 |
| 7,100,049 B2 | 8/2006 | Gasparini et al. | |
| 7,100,821 B2 | 9/2006 | Rasti | |
| 7,111,172 B1 | 9/2006 | Duane et al. | |
| 7,114,652 B2 | 10/2006 | Moullette et al. | |
| 7,136,514 B1 | 11/2006 | Wong | |
| 7,140,550 B2 | 11/2006 | Ramachandran | |
| 7,163,153 B2 | 1/2007 | Blossom | |
| 7,195,154 B2 | 3/2007 | Routhenstein | |
| 7,195,160 B2 | 3/2007 | Ison et al. | |
| 7,197,639 B1 | 3/2007 | Juels et al. | |
| 7,219,368 B2 | 5/2007 | Juels et al. | |
| 7,225,537 B2 | 6/2007 | Reed | |
| 7,225,994 B2 | 6/2007 | Finkelstein | |
| 7,246,752 B2 | 7/2007 | Brown | |
| 7,298,243 B2 | 11/2007 | Juels et al. | |
| 7,334,732 B2 | 2/2008 | Cooper | |
| 7,337,326 B2 | 2/2008 | Palmer et al. | |
| 7,346,775 B2 | 3/2008 | Gasparini et al. | |
| 7,347,382 B2 | 3/2008 | Ferber et al. | |
| 7,356,696 B1 | 4/2008 | Jakobsson et al. | |
| 7,357,319 B1 | 4/2008 | Lin et al. | |
| 7,359,507 B2 | 4/2008 | Kaliski | |
| 7,360,688 B1 | 4/2008 | Harris | |
| 7,363,494 B2 | 4/2008 | Brainard et al. | |
| 7,364,092 B2 | 4/2008 | Narendra et al. | |
| 7,380,710 B2 | 6/2008 | Brown | |
| 7,398,253 B1 | 7/2008 | Pinnell | |
| 7,404,087 B2 | 7/2008 | Teunen | |
| 7,424,570 B2 | 9/2008 | D'Albore et al. | |
| 7,427,033 B1 | 9/2008 | Roskind | |
| 7,454,349 B2 | 11/2008 | Teunen et al. | |
| 7,461,250 B1 | 12/2008 | Duane et al. | |
| 7,461,399 B2 | 12/2008 | Juels et al. | |
| 7,472,093 B2 | 12/2008 | Juels | |
| 7,472,829 B2 | 1/2009 | Brown | |
| 7,494,055 B2 | 2/2009 | Fernandes et al. | |
| 7,502,467 B2 | 3/2009 | Brainard et al. | |
| 7,502,933 B2 | 3/2009 | Jakobsson et al. | |
| 7,503,485 B1 | 3/2009 | Routhenstein | |
| 7,516,492 B1 | 4/2009 | Nisbet et al. | |
| 7,523,301 B2 | 4/2009 | Nisbet et al. | |
| 7,530,495 B2 | 5/2009 | Cooper | |
| 7,532,104 B2 | 5/2009 | Juels | |
| 7,543,739 B2 | 6/2009 | Brown et al. | |
| 7,559,464 B2 | 7/2009 | Routhenstein | |
| 7,562,221 B2 | 7/2009 | Nystrom et al. | |
| 7,562,222 B2 | 7/2009 | Gasparini et al. | |
| 7,580,898 B2 | 8/2009 | Brown et al. | |
| 7,584,153 B2 * | 9/2009 | Brown et al. | 705/75 |

| Patent/Publication | Date | Inventor | Class |
|---|---|---|---|
| 7,591,416 B2* | 9/2009 | Blossom | 235/380 |
| 7,591,426 B2* | 9/2009 | Osterweil et al. | 235/449 |
| 7,591,427 B2 | 9/2009 | Osterweil | |
| 7,602,904 B2 | 10/2009 | Juels et al. | |
| 7,621,458 B2 | 11/2009 | Zellner et al. | |
| 7,631,804 B2 | 12/2009 | Brown | |
| 7,639,537 B2 | 12/2009 | Sepe et al. | |
| 7,641,124 B2 | 1/2010 | Brown et al. | |
| 7,660,902 B2 | 2/2010 | Graham et al. | |
| 7,681,232 B2 | 3/2010 | Nordentoft et al. | |
| 7,828,207 B2 | 11/2010 | Cooper | |
| 7,954,708 B2* | 6/2011 | Blossom | 235/380 |
| 7,954,725 B2* | 6/2011 | Blythe | 235/493 |
| 7,988,061 B2* | 8/2011 | Cook et al. | 235/493 |
| 7,996,318 B2* | 8/2011 | Marcon | 705/50 |
| 2001/0009485 A1* | 7/2001 | Furuya | 360/88 |
| 2001/0017318 A1* | 8/2001 | Nagata et al. | 235/451 |
| 2001/0025885 A1* | 10/2001 | Kuroiwa et al. | 235/449 |
| 2001/0034702 A1 | 10/2001 | Mockett et al. | |
| 2001/0047335 A1 | 11/2001 | Arndt et al. | |
| 2002/0003169 A1 | 1/2002 | Cooper | |
| 2002/0032657 A1 | 3/2002 | Singh | |
| 2002/0043566 A1 | 4/2002 | Goodman et al. | |
| 2002/0059114 A1 | 5/2002 | Cockrill et al. | |
| 2002/0072931 A1 | 6/2002 | Card | |
| 2002/0082989 A1 | 6/2002 | Fife et al. | |
| 2002/0096570 A1 | 7/2002 | Wong et al. | |
| 2002/0120583 A1 | 8/2002 | Keresman, III et al. | |
| 2002/0153424 A1 | 10/2002 | Li | |
| 2003/0034388 A1 | 2/2003 | Routhenstein et al. | |
| 2003/0052168 A1 | 3/2003 | Wong | |
| 2003/0057278 A1 | 3/2003 | Wong | |
| 2003/0069846 A1* | 4/2003 | Marcon | 705/41 |
| 2003/0089774 A1 | 5/2003 | Schmieder et al. | |
| 2003/0111527 A1 | 6/2003 | Blossom | |
| 2003/0116635 A1 | 6/2003 | Taban | |
| 2003/0152253 A1 | 8/2003 | Wong | |
| 2003/0163287 A1 | 8/2003 | Vock et al. | |
| 2003/0173409 A1 | 9/2003 | Vogt et al. | |
| 2003/0179909 A1 | 9/2003 | Wong et al. | |
| 2003/0179910 A1 | 9/2003 | Wong | |
| 2003/0209608 A1 | 11/2003 | Blossom | |
| 2003/0218066 A1 | 11/2003 | Fernandes et al. | |
| 2003/0226899 A1 | 12/2003 | Finkelstein | |
| 2004/0011877 A1 | 1/2004 | Reppermund | |
| 2004/0026506 A1 | 2/2004 | Finkelstein | |
| 2004/0035942 A1 | 2/2004 | Silverman | |
| 2004/0089723 A1* | 5/2004 | Moriya | 235/475 |
| 2004/0133787 A1* | 7/2004 | Doughty et al. | 713/186 |
| 2004/0159700 A1 | 8/2004 | Khan et al. | |
| 2004/0162732 A1 | 8/2004 | Rahim et al. | |
| 2004/0172535 A1 | 9/2004 | Jakobsson | |
| 2004/0177045 A1 | 9/2004 | Brown | |
| 2004/0251303 A1* | 12/2004 | Cooper | 235/380 |
| 2005/0001711 A1 | 1/2005 | Doughty et al. | |
| 2005/0006482 A1* | 1/2005 | Kano et al. | 235/488 |
| 2005/0043997 A1 | 2/2005 | Sohata et al. | |
| 2005/0080747 A1 | 4/2005 | Anderson et al. | |
| 2005/0086160 A1 | 4/2005 | Wong et al. | |
| 2005/0086177 A1 | 4/2005 | Anderson et al. | |
| 2005/0092830 A1 | 5/2005 | Blossom | |
| 2005/0116026 A1 | 6/2005 | Burger et al. | |
| 2005/0119940 A1 | 6/2005 | Concilio et al. | |
| 2005/0133590 A1 | 6/2005 | Rettenmyer et al. | |
| 2005/0154643 A1 | 7/2005 | Doan et al. | |
| 2005/0178827 A1 | 8/2005 | Shatford | |
| 2005/0194452 A1 | 9/2005 | Nordentoft et al. | |
| 2005/0211785 A1* | 9/2005 | Ferber et al. | 235/492 |
| 2005/0218229 A1 | 10/2005 | Morley et al. | |
| 2005/0219728 A1* | 10/2005 | Durbin et al. | 360/46 |
| 2005/0228959 A1 | 10/2005 | D'Albore et al. | |
| 2006/0000900 A1 | 1/2006 | Fernandes et al. | |
| 2006/0000918 A1 | 1/2006 | Kano et al. | 235/492 |
| 2006/0017570 A1* | 1/2006 | Moskowitz et al. | 340/572.7 |
| 2006/0037073 A1 | 2/2006 | Juels et al. | |
| 2006/0041759 A1 | 2/2006 | Kaliski et al. | |
| 2006/0043180 A1 | 3/2006 | Ison et al. | |
| 2006/0085328 A1 | 4/2006 | Cohen et al. | |
| 2006/0091223 A1 | 5/2006 | Zellner | |
| 2006/0131393 A1 | 6/2006 | Cok et al. | |
| 2006/0131396 A1* | 6/2006 | Blossom | 235/380 |
| 2006/0131410 A1 | 6/2006 | Fernandes et al. | |
| 2006/0161435 A1 | 7/2006 | Atef et al. | |
| 2006/0161789 A1 | 7/2006 | Doughty et al. | |
| 2006/0163353 A1 | 7/2006 | Moulette et al. | |
| 2006/0174104 A1 | 8/2006 | Crichton et al. | |
| 2006/0186209 A1 | 8/2006 | Narendra et al. | |
| 2006/0196931 A1 | 9/2006 | Holtmanns et al. | |
| 2006/0226224 A1 | 10/2006 | Henry | |
| 2006/0227523 A1* | 10/2006 | Pennaz et al. | 361/783 |
| 2006/0249574 A1 | 11/2006 | Brown et al. | |
| 2006/0256961 A1 | 11/2006 | Brainard et al. | |
| 2006/0261174 A1 | 11/2006 | Zellner et al. | |
| 2006/0283958 A1* | 12/2006 | Osterweil | 235/492 |
| 2007/0017975 A1 | 1/2007 | Lewis et al. | |
| 2007/0023532 A1 | 2/2007 | Narendra et al. | |
| 2007/0034700 A1* | 2/2007 | Poidomani et al. | 235/492 |
| 2007/0114274 A1 | 5/2007 | Gibbs et al. | |
| 2007/0124321 A1 | 5/2007 | Szydlo | |
| 2007/0131759 A1 | 6/2007 | Cox et al. | |
| 2007/0131768 A1* | 6/2007 | Wakabayashi | 235/449 |
| 2007/0136211 A1 | 6/2007 | Brown et al. | |
| 2007/0152070 A1 | 7/2007 | D'Albore | |
| 2007/0152072 A1 | 7/2007 | Frallicciardi et al. | |
| 2007/0153487 A1 | 7/2007 | Frallicciardi et al. | |
| 2007/0174614 A1 | 7/2007 | Duane et al. | |
| 2007/0192249 A1 | 8/2007 | Biffle et al. | |
| 2007/0241183 A1 | 10/2007 | Brown et al. | |
| 2007/0241201 A1 | 10/2007 | Brown et al. | |
| 2007/0256123 A1 | 11/2007 | Duane et al. | |
| 2007/0290049 A1* | 12/2007 | Ratcliffe | 235/492 |
| 2007/0291753 A1 | 12/2007 | Romano | |
| 2008/0005510 A1 | 1/2008 | Sepe et al. | |
| 2008/0008315 A1 | 1/2008 | Fontana et al. | |
| 2008/0008322 A1 | 1/2008 | Fontana et al. | |
| 2008/0010675 A1 | 1/2008 | Massascusa et al. | |
| 2008/0016351 A1 | 1/2008 | Fontana et al. | |
| 2008/0019507 A1 | 1/2008 | Fontana et al. | |
| 2008/0028447 A1 | 1/2008 | O'Malley et al. | |
| 2008/0040271 A1 | 2/2008 | Hammad et al. | |
| 2008/0040276 A1 | 2/2008 | Hammad et al. | |
| 2008/0058016 A1 | 3/2008 | Di Maggio et al. | |
| 2008/0059379 A1* | 3/2008 | Ramaci et al. | 705/66 |
| 2008/0093467 A1 | 4/2008 | Narendra et al. | |
| 2008/0096326 A1 | 4/2008 | Reed | |
| 2008/0116283 A1* | 5/2008 | Newbrough et al. | 235/487 |
| 2008/0121726 A1* | 5/2008 | Brady et al. | 235/493 |
| 2008/0126260 A1 | 5/2008 | Cox et al. | |
| 2008/0126398 A1 | 5/2008 | Cimino | |
| 2008/0128515 A1 | 6/2008 | Di Iorio | |
| 2008/0148394 A1 | 6/2008 | Poidomani et al. | |
| 2008/0201264 A1 | 8/2008 | Brown et al. | |
| 2008/0209550 A1 | 8/2008 | Di Iorio | |
| 2008/0223937 A1 | 9/2008 | Preta et al. | |
| 2008/0288699 A1 | 11/2008 | Chichierchia | |
| 2008/0290166 A1 | 11/2008 | von Mueller | |
| 2008/0294930 A1 | 11/2008 | Varone et al. | |
| 2008/0302877 A1 | 12/2008 | Musella et al. | |
| 2008/0314976 A1 | 12/2008 | Capurso et al. | |
| 2009/0006262 A1 | 1/2009 | Brown et al. | |
| 2009/0013122 A1 | 1/2009 | Sepe et al. | |
| 2009/0036147 A1 | 2/2009 | Romano | |
| 2009/0046522 A1 | 2/2009 | Sepe et al. | |
| 2009/0048971 A1* | 2/2009 | Hathaway et al. | 705/41 |
| 2009/0055893 A1 | 2/2009 | Manessis et al. | |
| 2009/0108064 A1 | 4/2009 | Fernandes et al. | |
| 2009/0150295 A1 | 6/2009 | Hatch et al. | |
| 2009/0152365 A1* | 6/2009 | Li et al. | 235/493 |
| 2009/0159680 A1* | 6/2009 | Mullen et al. | 235/449 |
| 2009/0164380 A1 | 6/2009 | Brown | |
| 2009/0166435 A1* | 7/2009 | Blythe | 235/493 |
| 2009/0240592 A1 | 9/2009 | Baumgart et al. | |
| 2009/0242648 A1 | 10/2009 | Di Sirio et al. | |
| 2009/0244858 A1 | 10/2009 | Di Sirio et al. | |
| 2009/0253460 A1 | 10/2009 | Varone et al. | |
| 2009/0255996 A1 | 10/2009 | Brown et al. | |
| 2009/0261161 A1* | 10/2009 | Blossom | 235/380 |
| 2009/0261167 A1* | 10/2009 | Iwayama | 235/454 |

| | | | |
|---|---|---|---|
| 2009/0290704 A1 | 11/2009 | Cimino | |
| 2009/0303885 A1 | 12/2009 | Longo | |
| 2010/0023453 A1* | 1/2010 | Keresman et al. | 705/41 |
| 2010/0084476 A1* | 4/2010 | Zellner et al. | 235/492 |
| 2010/0127830 A1* | 5/2010 | Nielsen et al. | 340/10.1 |
| 2010/0270373 A1* | 10/2010 | Poidomani et al. | 235/380 |
| 2011/0028184 A1* | 2/2011 | Cooper | 455/556.1 |
| 2011/0108626 A1 | 5/2011 | Hepner et al. | |
| 2011/0174874 A1* | 7/2011 | Poznansky et al. | 235/379 |
| 2011/0240748 A1* | 10/2011 | Doughty et al. | 235/492 |
| 2011/0266354 A1* | 11/2011 | Poidomani et al. | 235/492 |
| 2011/0269438 A1* | 11/2011 | Narendra et al. | 455/414.1 |

FOREIGN PATENT DOCUMENTS

| | | |
|---|---|---|
| GB | 2420098 | 5/2006 |
| JP | 60219636 A * | 11/1985 |
| JP | 05210770 A | 8/1993 |
| WO | WO9852735 | 11/1998 |
| WO | WO0247019 | 6/2002 |
| WO | WO2006066322 | 6/2006 |
| WO | WO2006080929 | 8/2006 |
| WO | WO2006105092 | 10/2006 |
| WO | WO2006116772 | 11/2006 |
| WO | WO2007141779 | 12/2007 |
| WO | WO2008064403 | 6/2008 |

OTHER PUBLICATIONS

U.S. Appl. No. 60/675,388, filed Apr. 27, 2005, Poidomani et al.
The Bank Credit Card Business. Second Edition, American Bankers Association, Washington, D.C., 1996.
A Day in the Life of a Flux Reversal. http://www.phrack/org/issues.html?issue=37&id=6#article. As viewed on Apr. 12, 2010.
Dynamic Virtual Credit Card Numbers. http://homes.cerias.purdue.edu/~jtli/paper/fc07.pdf. As viewed on Apr. 12, 2010.
USPTO, International Search Report, Apr. 28, 2009.
English translation of JP 05210770 A.
Extended European Search Report, Jan. 26, 2012.

* cited by examiner

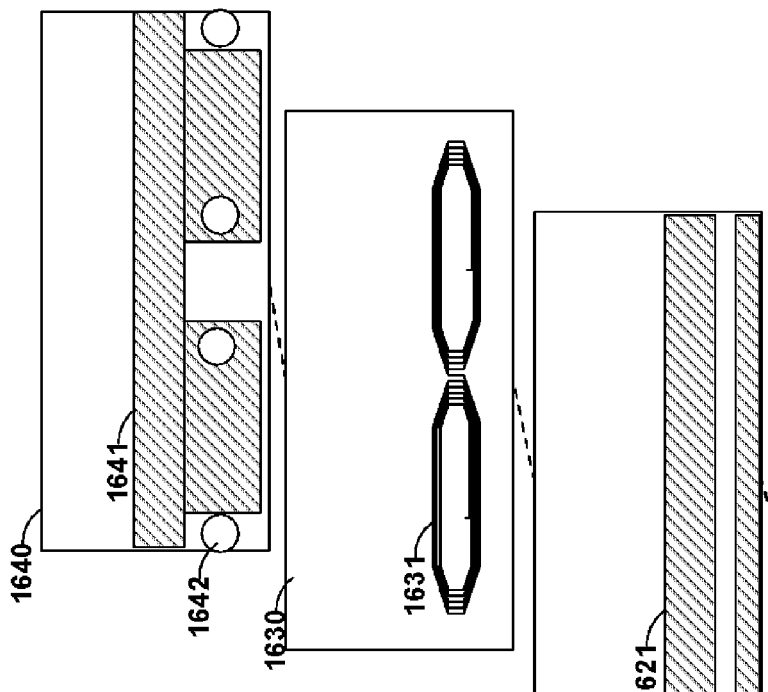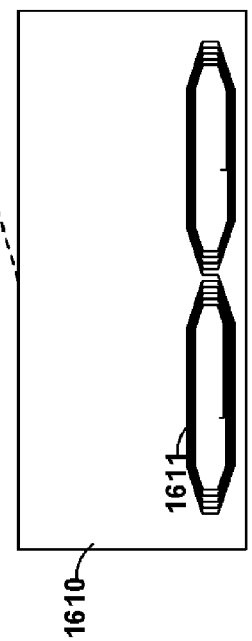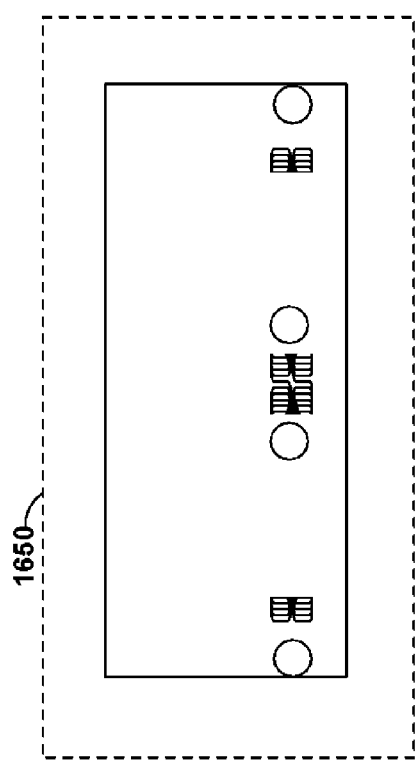
FIG. 16

CARDS AND DEVICES WITH MAGNETIC EMULATORS AND MAGNETIC READER READ-HEAD DETECTORS

CROSS-REFERENCE TO RELATED APPLICATIONS

This application is a continuation of U.S. patent application Ser. No. 12/339,046, filed on Dec. 19, 2008, which claims the benefit of U.S. Provisional Patent Application Nos. 61/016,491 filed on Dec. 24, 2007, No. 61/026,846 filed on Feb. 7, 2008, No. 61/027,807 filed on Feb. 11, 2008, No. 61/081,003 filed on Jul. 15, 2008, No. 61/086,239 filed on Aug. 5, 2008, No. 61/090,423 filed on Aug. 20, 2008, No. 61/097,401 filed Sep. 16, 2008, No. 61/112,766 filed on Nov. 9, 2008, No. 61/117,186 filed on Nov. 23, 2008, No. 61/119,366 filed on Dec. 2, 2008, and No. 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Magnetic emulation circuits may be provided that generate electromagnetic fields. The emulation circuits may have active regions operable to be read by a read-head of a magnetic stripe reader. The emulation circuits may also have, for example, non-active regions that are not operable to be read by a read-head of a magnetic stripe reader. Multiple emulation circuits may be provided on different layers such that the active regions of multiple emulation circuits provide a read-head of a magnetic stripe reader continuous visibility to active regions while a card is swiped.

Magnetic emulation circuits may extend across multiple tracks. However, the areas of such magnetic emulation circuits that extended to undesired tracks may be configured to be invisible to the read-heads for those tracks. For example, a magnetic emulator may produce magnetic fields that are not oriented properly to be picked up by unintended read-head(s) but that are oriented properly to be picked up by intended read-head(s).

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 16 is an illustration of a card constructed in accordance with the principles of the present invention;

DETAILED DESCRIPTION OF THE INVENTION

Figure 1:
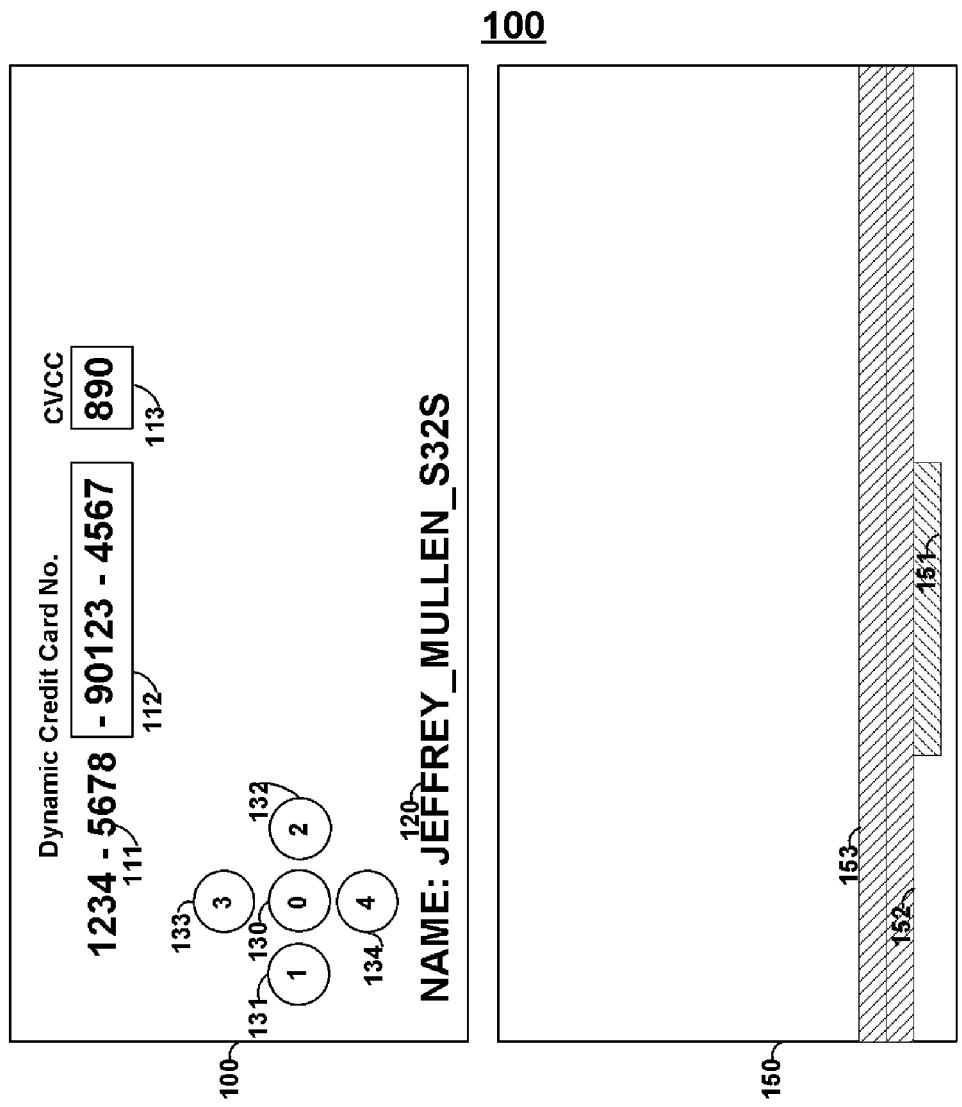
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card. Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identifies using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. A magnetic emulator may be provided as device 151. Device 151 may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 Khz).

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Device 151 may include an emulator such that dynamic information may be communicated through emulator 151. Any combination of emulators and static magnetic tracks may be utilized for a card or device.

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
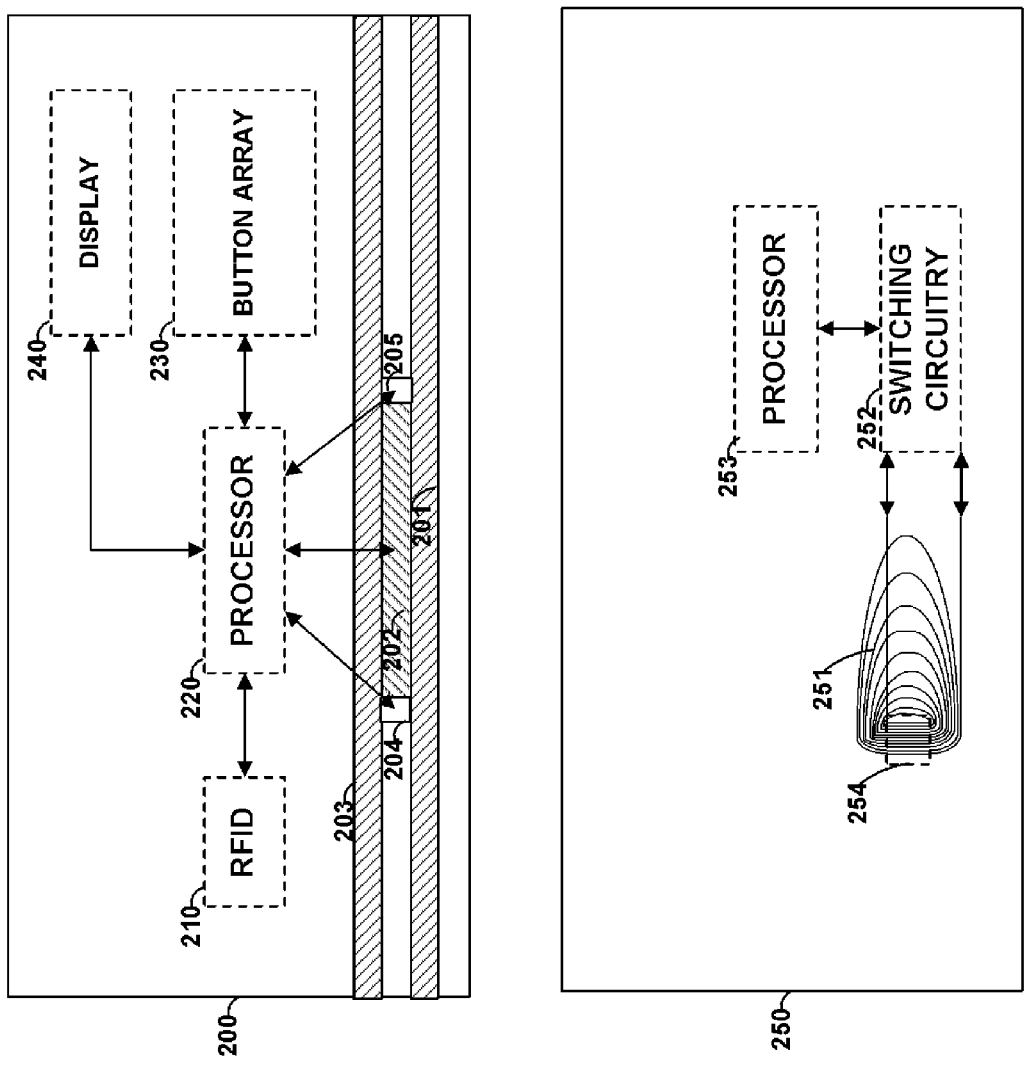
FIG. 2 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202.

Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes active region 254 operable to communicate data serially to a magnetic stripe reader. Similarly, for example, emulator 251 may receive information for a magnetic stripe encoder. Persons skilled in the art will appreciate that emulator 251 includes a tail that is spread-out. Such a tail may include the return lines of emulator 251 and may be spaced such that a magnetic reader is not able to pick up the electromagnetic fields generated by such a tail. Accordingly, active region 254 may be spaced close together such that a magnetic stripe reader is able to pick up the cumulative electromagnetic field generated by such an active region. Processor 253 may drive emulator 251 via switching circuitry 252. Switching circuitry 252 may include, for example, one or more transistors that may be utilized to control the direction of current via emulator 251 (e.g., the polarity of voltage(s) across a drive resistor).

Figure 3:
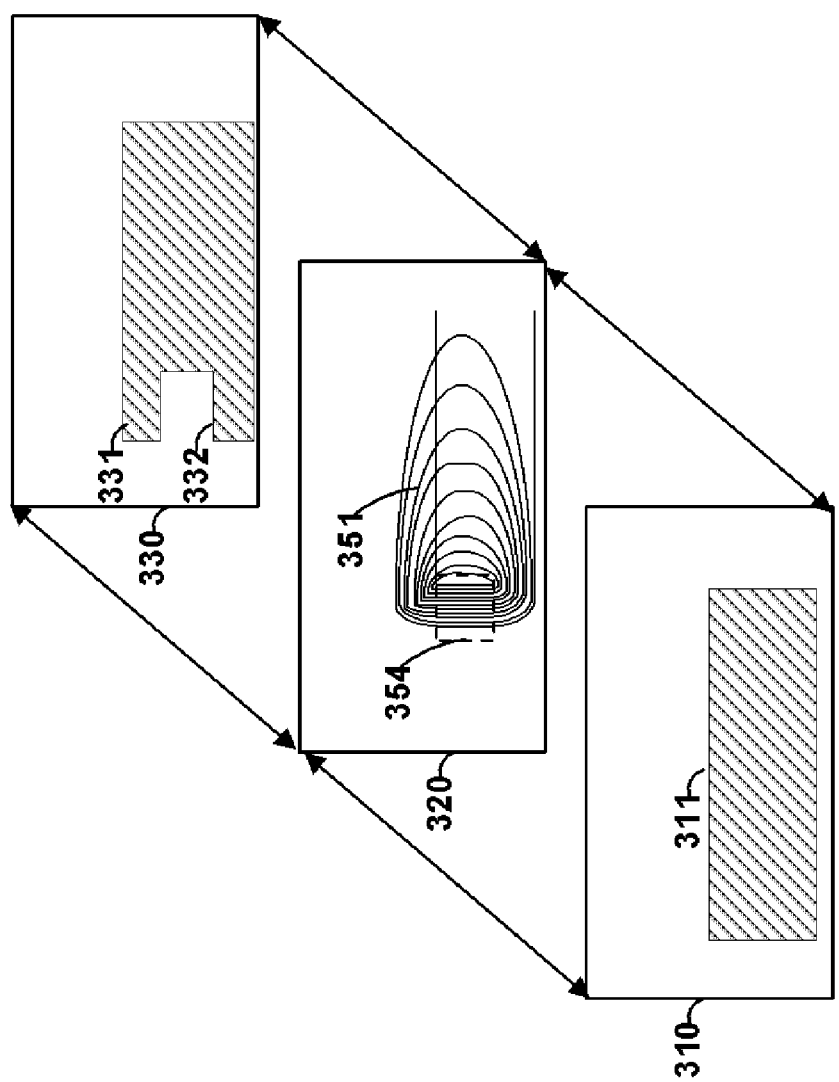
FIG. 3 is an illustration of a card constructed in accordance with the principles of the present invention.

Magnetic shielding may be provided to limit an electromagnetic field of an emulator. For example, layer 310 of FIG. 3 may include magnetic shielding 311 (which may be a magnetic material). Magnetic shielding may block magnetic fields from emulator 351 on layer 320. Accordingly, for example, a card may not interact with read-heads blocked from emulator 351 from magnetic shielding 311. In doing so, for example, a magnetic stripe reader may receive information from a single read-head of a read-head housing at any given time. Layer 330 may be provided, for example, with magnetic shielding 331 that includes an active-region space 332. Accordingly, layer 330 may block magnetic fields from emulator 351 except for those fields generated by active portion 354 (e.g., if space 332 is aligned with active potion 354).

Figure 4:
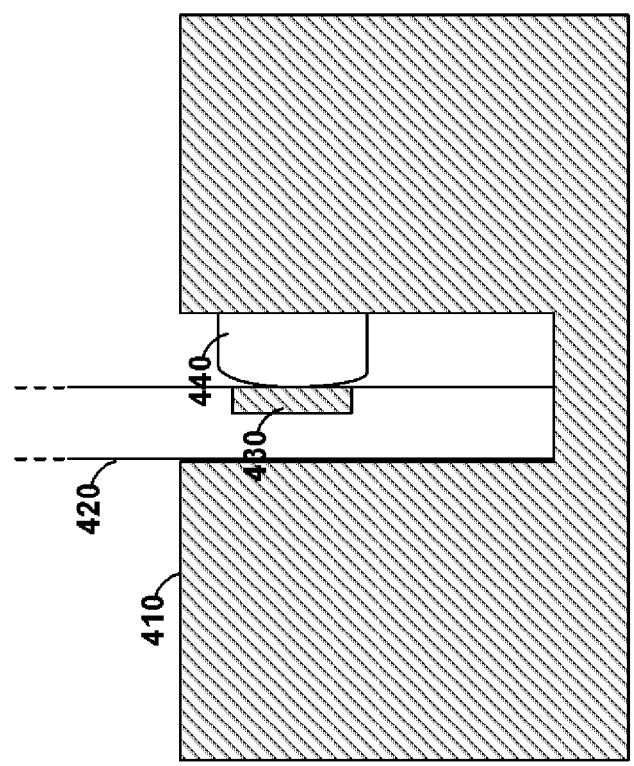
FIG. 4 is an illustration of a card and a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
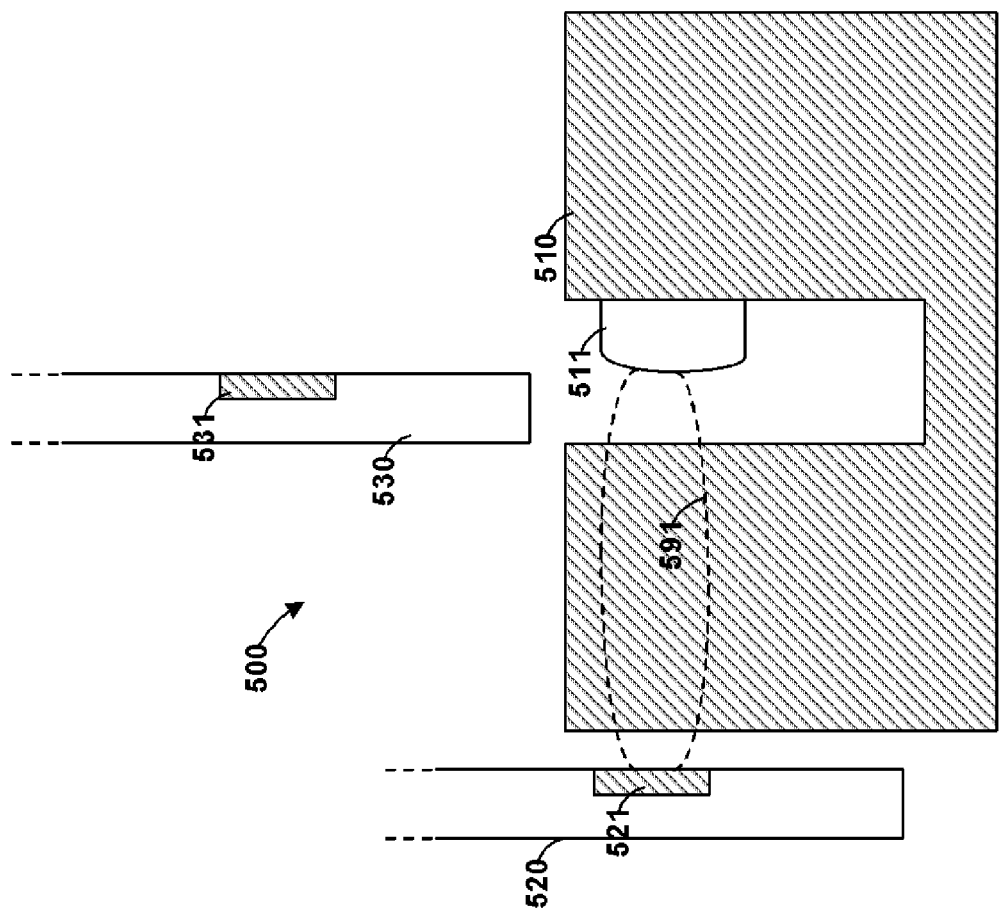
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contact-less transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Figure 6:
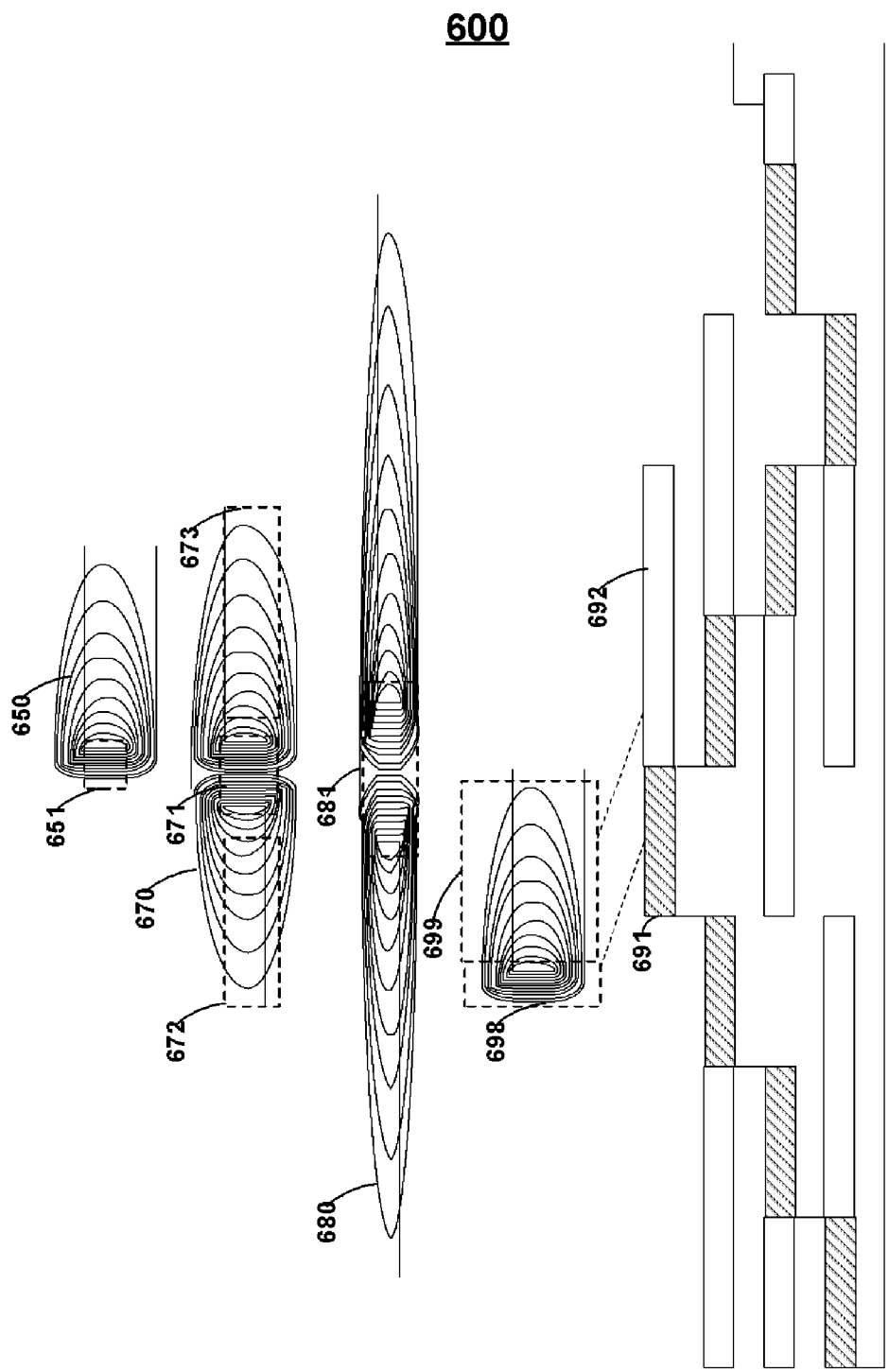
FIG. 6 is an illustration of a circuit constructed in accordance with the principles of the present invention.

FIG. 6 includes circuits 600 that may include magnetic emulator 650 that includes active region 651. Magnetic emulator 650 may be, for example, a coil. Current may be provided through magnetic emulator 650 such that the magnetic emulator generates an electromagnetic signal. Active region 651 may include a dense section of coil segments where current runs through those coil segments in the same direction. Accordingly, the electromagnetic field is intensified in active region 651 compared to the area of the coil with coil segments that are widely spaced. Accordingly, a current may be placed through the coil such that a magnetic stripe reader is operable to receive information from active region 651 but not the region outside active region 651. Persons skilled in the art will appreciate that the direction of current through magnetic circuit 650 may be reversed in a pattern that is representative of magnetic stripe data. Particularly, a processor may, for example, transmit information through a coil by changing the direction of the electromagnetic field generated from emulator circuit 650 at particular times. A change in the frequency of field reversals may be representative of, for example, a particular bit of information (e.g., "1" or "0"). Magnetic emulation circuit 650 may include a dense active region and a less dense tail region.

Magnetic emulation circuit 670 may be included that includes active region 671 and non-active regions 672 and 673. Active region 671 may include coil segments in which current flows through the segments in the same direction. Non-active regions 672 and 673 may include, for example, coil segment spacing that is wider than the coil segment spacing of active regions 671. Persons skilled in the art will appreciate, for example, that non-active regions 672 and 673 may be utilized to communicate information to a magnetic stripe reader. However, active region 671 may include a stronger electromagnetic signal then non-active regions 672 and 673. Persons skilled in the art will also appreciate that a read-head may travel through non-active region 672, through active region 671, and through non-active region 673 when reading information communicated from emulator circuit 670. Persons skilled in the art will appreciate that the level of current provided to emulator circuit 670 may be configured such that a magnetic read-head received information from active region 671 but does not receive information from non-active regions 672 and 673. Emulator 670 may, for example, be tall enough such that more than one read-head passes over emulator 670 at any one time. For example, one read-head from a magnetic stripe reader may pass over active region 671 and another read-head from a magnetic stripe reader may pass under active region 671. Person skilled in the art will appreciate that coil segments may be configured in an orientation such that they produce electromagnetic fields that are invisible to such read-heads. For example, active region 671 may include coil segments that are parallel to one another. Coil segments above and below active region 671 may be configured to be perpendicular to the coil segments of active region 671 or approximately oriented at a 45 degree angle from the coil segments of active region 671.

Magnetic emulation circuit 680 may be provided that includes active region 681. Persons skilled in the art will appreciate, for example, that the height of magnetic emulation circuit 680 may be approximately equal to the height of a read-head of a magnetic stripe reader such that, for example, only one track read-head, of a multiple track read-head housing, passes over magnetic emulation circuit 680.

Multiple magnetic emulation circuits may be provided on a multiple layer PCB. For example, a magnetic emulation circuit may be provided with active region 691 (e.g., active region 698) and non-active region 692 (e.g., non-active region 699). Emulators may be provided on different layers such that active layers align with non-active layers. Accordingly, for example, a read-head may pick up a continuous stream of active regions. Accordingly, the active regions may be controlled through a common switching circuit such that current flows in the same direction through the active regions of the multiple layer PCB at a given time. Accordingly, the active regions may, for example, provide electromagnetic fields in the same direction. Persons skilled in the art will appreciate that the widths of coil segments of non-active regions may be widened to decrease the effect of those non-active regions when multiple non-active regions are stacked. Additionally, for example, the coil segments of vertically stacked non-active regions may be aligned with one another or may be staggered from one another. Furthermore, for example, current may flow through vertically stacked non-active regions in the same or different directions.

Figure 7:
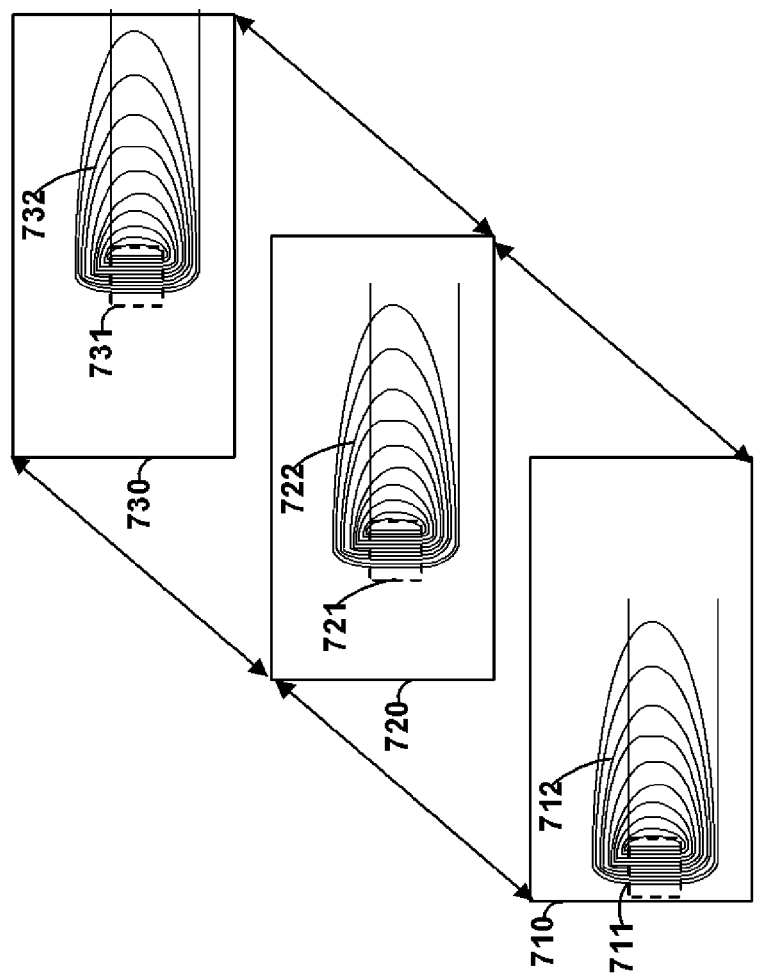
FIG. 7 is an illustration of a circuit constructed in accordance with the principles of the present invention.

FIG. 7 shows card 700 that may include layers 710, 720, and 730 fabricated as, for example, flexible PCB layers. Layer 710 may include, for example, magnetic emulation circuit 712 that includes active region 711. Layer 720 may include, for example, magnetic emulation circuit 722 that may include active region 721. Layer 730 may include magnetic emulation circuit 732 that may include active region 731.

Figure 8:
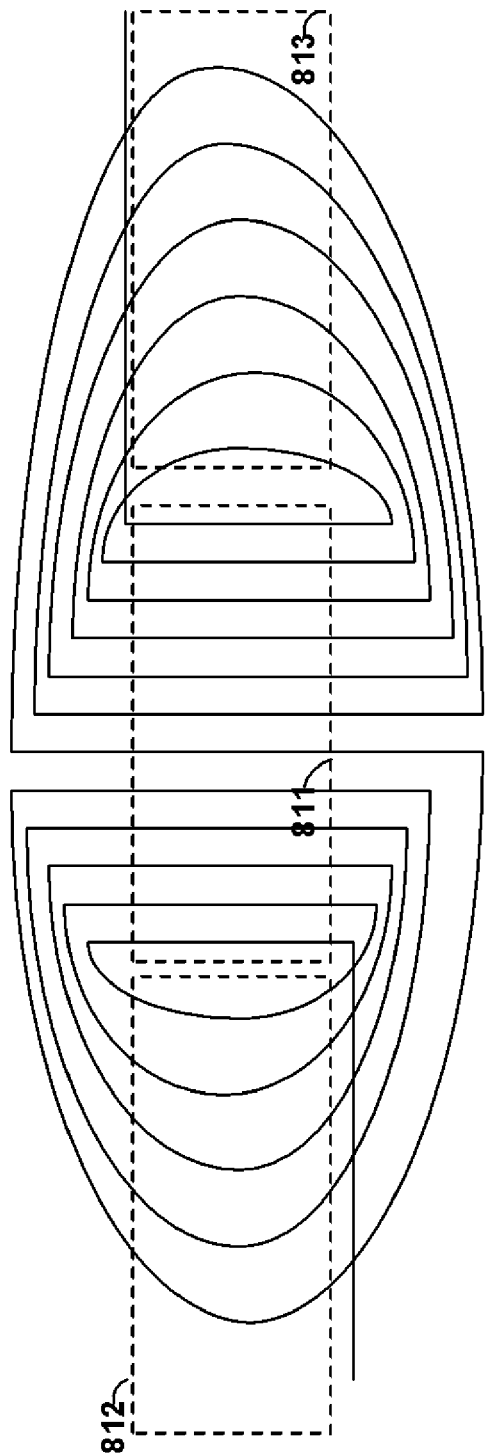
FIG. 8 is an illustration of a circuit constructed in accordance with the principles of the present invention.

FIG. 8 includes circuit 800 that may include, for example, active-region 811 and non-active regions 812 and 813.

Figure 9:
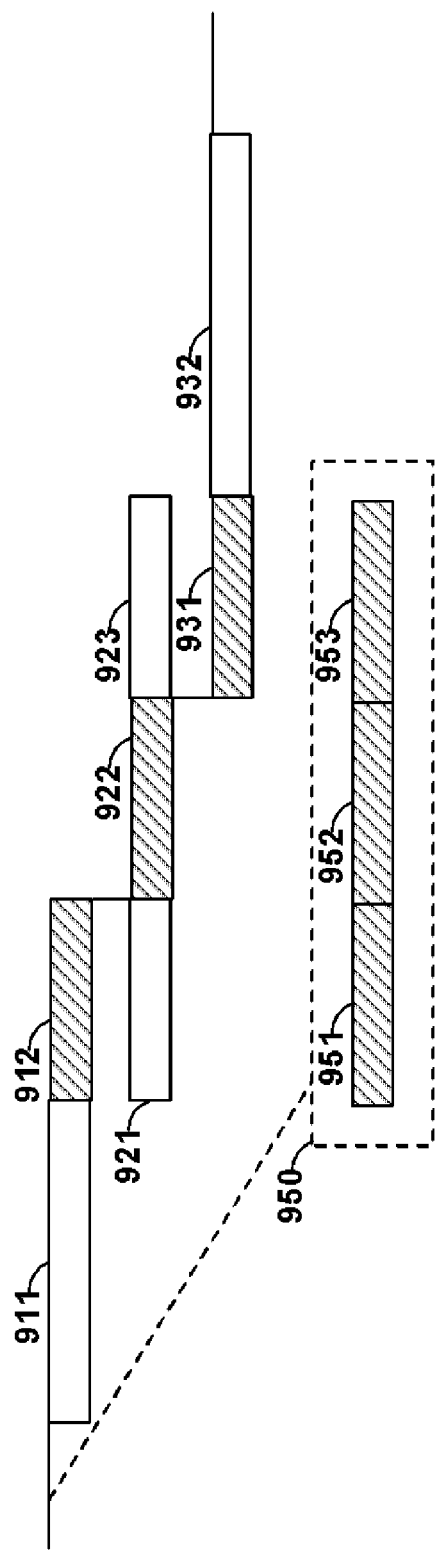
FIG. 9 is an illustration of a circuit constructed in accordance with the principles of the present invention.

Persons skilled in the art will appreciate that magnetic emulation circuits with one non-active region may be vertically stacked with magnetic emulation circuits with two non-active regions. Magnetic emulation circuits with one non-active region may have non-active regions that are wider than the non-active regions of a magnetic emulation circuit with two non-active regions. FIG. 9 shows topology 900 that may include active region 912 (e.g., active region 951), active region 922 (e.g., active region 952), and active region 931 (e.g., active region 953). Non-active regions 911, 921, 923, and 932 may also be included.

Figure 10:
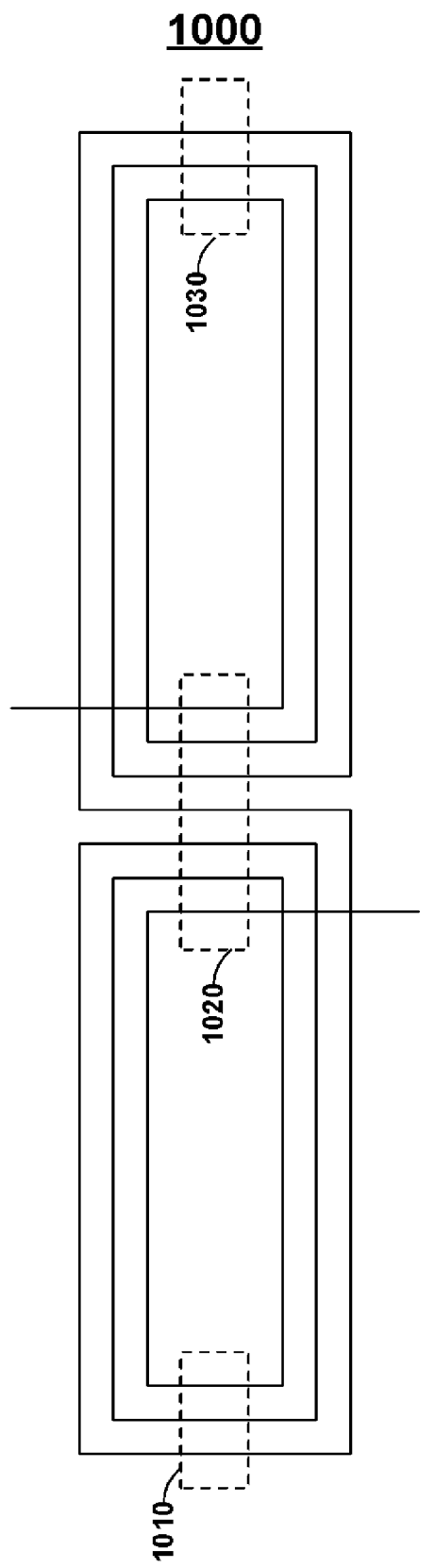
FIG. 10 is an illustration of a circuit constructed in accordance with the principles of the present invention.

FIG. 10 shows magnetic emulation circuit 1000 that may include region 1010, 1020, and 1030. Regions 1010, 1020, and 1030 may include approximately the same spacing between coil segments or may provide different spacing between coil segments.

Figure 11:
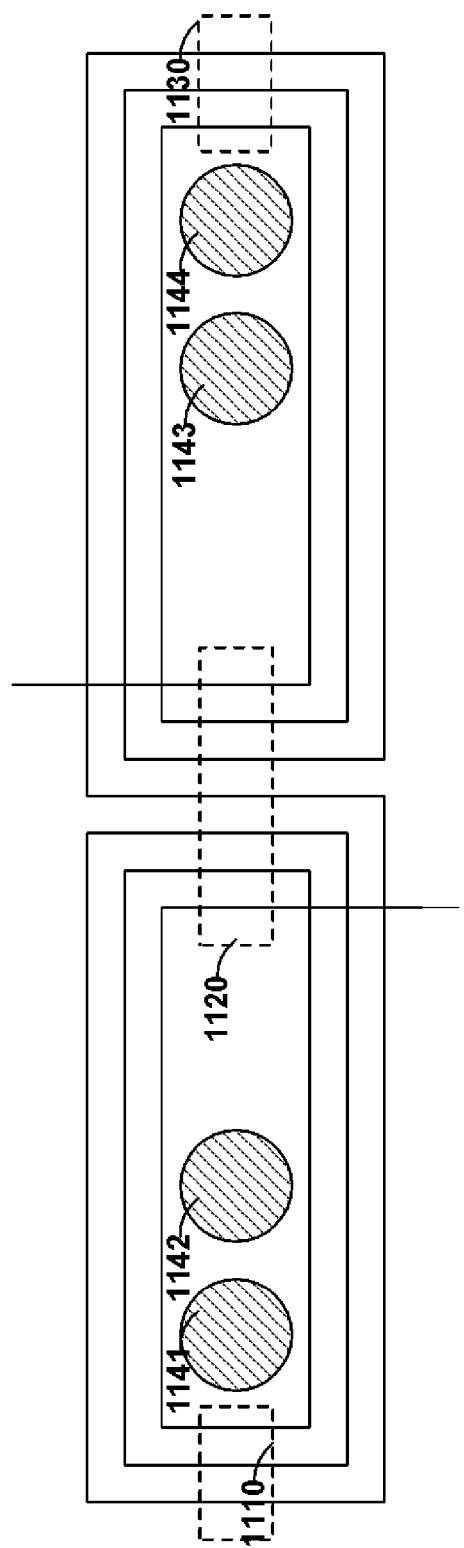
FIG. 11 is an illustration of a circuit constructed in accordance with the principles of the present invention.

FIG. 11 shows circuit 1100 that may include region 1110, 1120, and 1130. Circuit 1100 may also include read-head detectors 1141, 1142, 1143, and 1144. Read-head detectors 1141, 1142, 1143, and 1144 may detect a read-head and/or a read-head housing of a magnetic stripe reader. A read-head detector may determine the presence of a read-head and/or read-head housing by detecting, for example, physical contact with a read-head and/or housing. Capacitive coupling, sonar, optical, or any other technique may be utilized to determine the presence of a read-head or read-head detector. Accordingly, for example, region 1020 may be utilized to communicate information to a magnetic stripe reader upon the detection of a read-head by a read-head detector. Accordingly, for example, no current may be provided through regions 1010 and 1030 when a read-head passes over regions 1010 and 1030. Multiple read-heads may be utilized, for example, to determine the direction that a read-head is moving as well as the read-heads velocity and/or acceleration. Such information may be utilized, for example, to provide information in different ways. For example, a processor may transmit information at a first rate when a user swipes a card including circuit 1100 at a first velocity and the processor may transmit the same (or different) information at a second rate when that user swipes the card at a second velocity.

Figure 12:
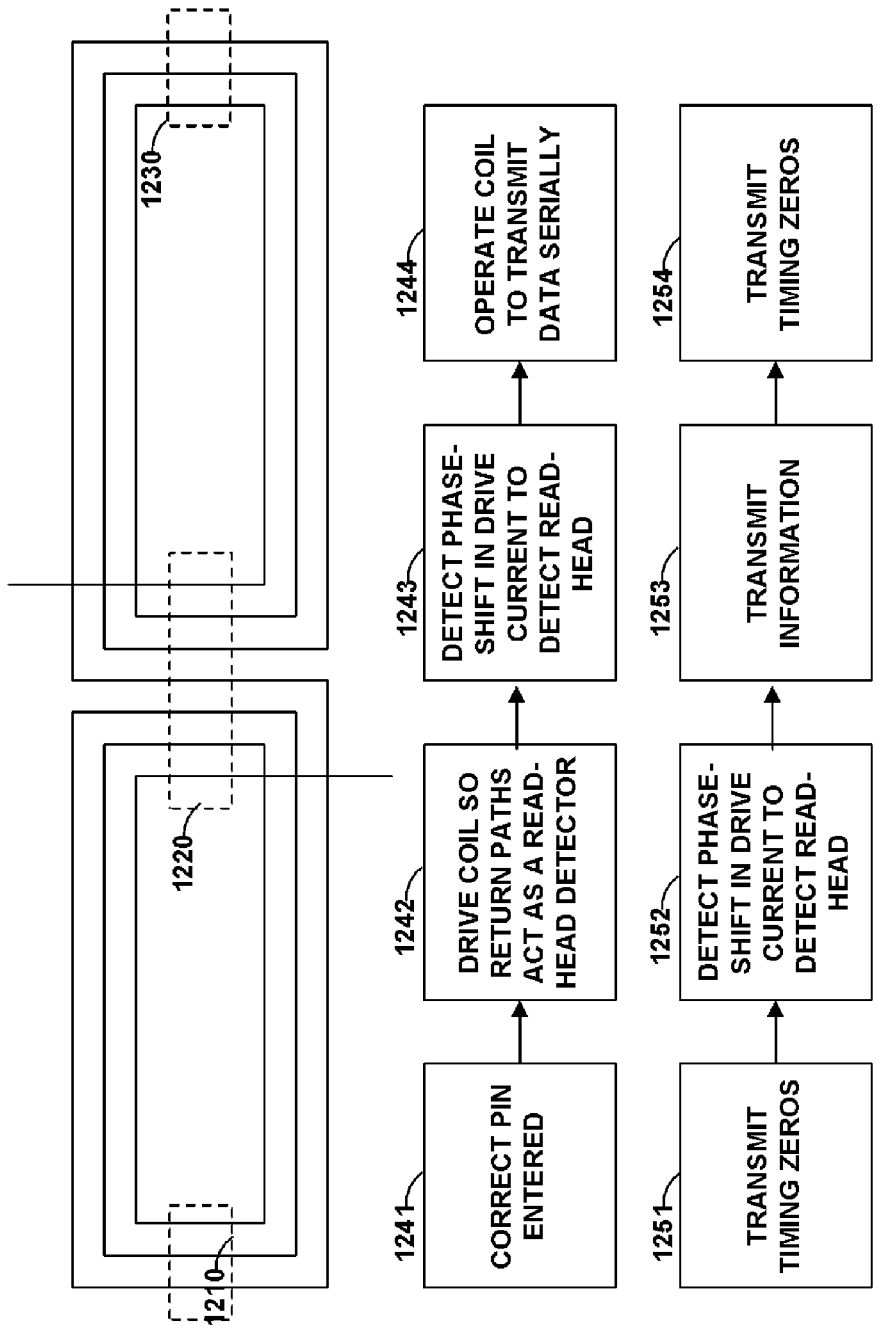
FIG. 12 is an illustration of a circuit and flow charts constructed in accordance with the principles of the present invention.

FIG. 12 shows topology 1200 that may include a magnetic emulation circuit having regions 1210, 1220, and 1230. Persons skilled in the art will appreciate that a magnetic emulation circuit may act as a read-head detector as well as a magnetic information transmitter. For example, a magnetic emulator may be driven according to a process that includes step 1241, in which a correct Personal Identification Code (e.g., a PIN) is determined to have been entered on a card. Accordingly, step 1242 may activate, in which a coil is driven such that its return paths act as a read-head detector. This may be done in numerous ways. For example, the current providing an electromagnetic field may undergo a phase-shift when a magnetic and/or conductive material is placed in the electromagnetic field. Accordingly, a phase-shift may be determined in step 1243. When such a phase-shift is determined, step 1244 may initiate and a magnetic emulation circuit may be driven to communicate data serially. Accordingly, regions 1210 and 1230 may be utilized to detect a read-head and region 1220 may be utilized to communicate information to that read-head. Persons skilled in the art will appreciate that a magnetic emulation circuit may not be supplied current until an appropriate Personal Identification Code (PIC) is entered into manual interfaces located on the card. Such a scheme, for example, provides for power savings as well as prevents card cloning. Accordingly, a magnetic emulator may be driven into a read-head detector mode upon receiving an appropriate manual input and then into a data transmission mode after determining the presence of a read-head.

Persons skilled in the art will appreciate that timing zeros may be provided before and after data such that a magnetic stripe reader can utilize such timing zeros to perform synchronization activities. Accordingly, a magnetic stripe emulator may transmit zeros while in a read-head detector mode in step 1251 and upon the detection of a current phase-shift in step 1252 the magnetic emulation circuit may transmit information in step 1253. After the data is transmitted, timing zeros may be transmitted again in step 1254. Step 1253 may also detect the presence of a read-head to determine, for example, whether all of the information was received. If a read-head was not detected after data transmission, the processor may increase the rate of data transmission for future transmissions until, for example, read-heads are detected at the beginning and the end of the transmission of data.

Persons skilled in the art will appreciate that a card may include multiple magnetic emulation and read-head detectors circuits. In this manner, a card may include multiple circuits that can operate as both a data transmitter and a read-head detector.

Figure 13:
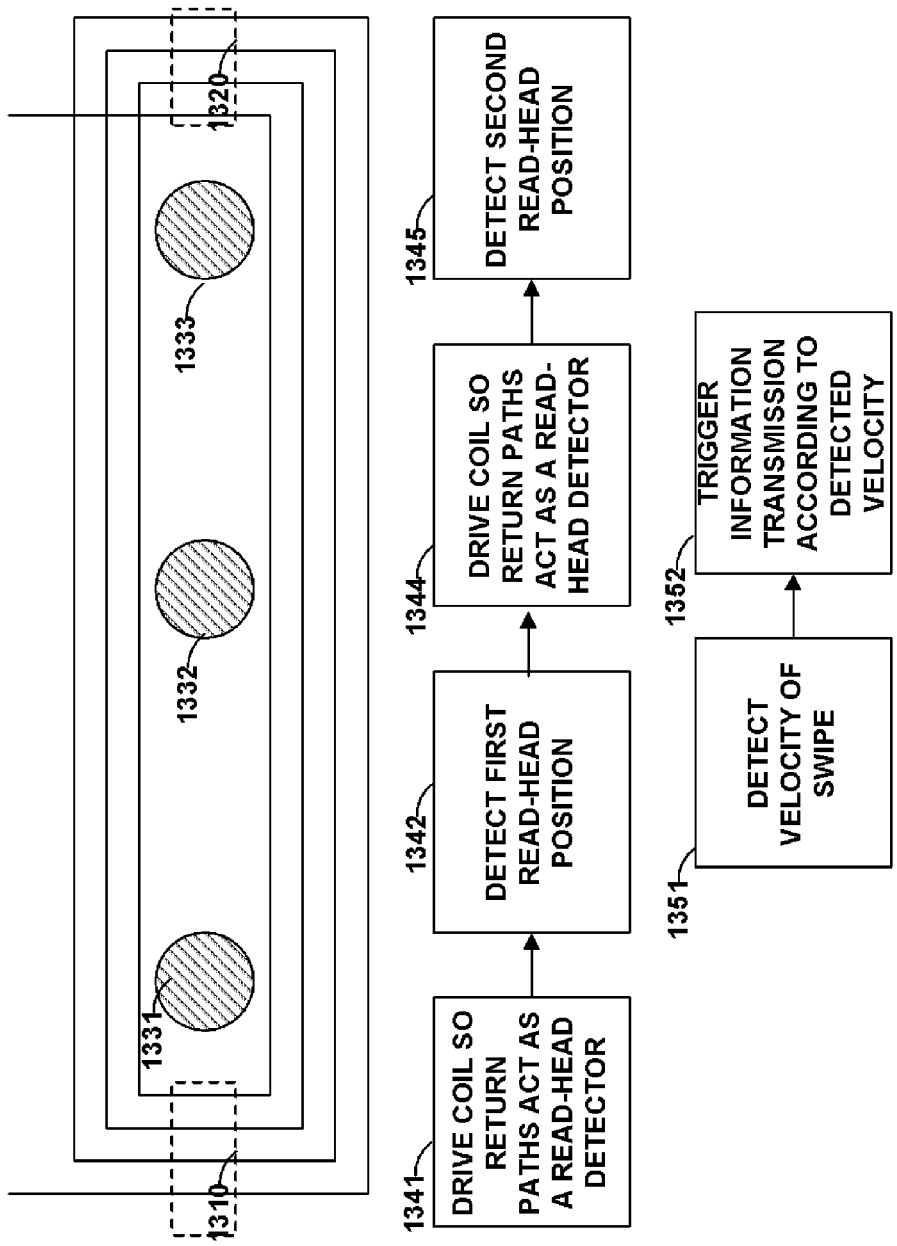
FIG. 13 is an illustration of a circuit and flow charts constructed in accordance with the principles of the present invention.

FIG. 13 includes topology 1300 that may include, for example, a magnetic emulation circuit that includes regions 1310 and 1320. Read-head detectors 1331, 1332, and 1332 may also be included.

A region (e.g., region 1310) may be utilized to determine the velocity of a read-head. For example, step 1341 may be included in which a region is driven such that the region acts as a read-head detector. A read-head may be detected in 1342, but the region may continue to drive the region to act as a read-head detector in step 1344. A second read-head position may then be determined in step 1345. The number of times that a read-head is sensed by a detector may correlate to a velocity. Information may then be transmitted (e.g., via another region) depending on the determined velocity. For example, the velocity of a swipe may be detected in step 1351 and information may be transmitted according to this velocity in step 1352. Read-head detectors 1331, 1332, and 1333 may also be utilized, for example, to determine the velocity of a read-head as well as the direction of movement of the read-head. Persons skilled in the art will appreciate that a magnetic stripe reader may be motorized and may read a card at a pre-determined speed. Such a card may determine that the card is being read by a motorized reader and may utilize this information to transmit different information and/or transmit information in a different manner.

Figure 14:
FIG. 14 is an illustration of a card constructed in accordance with the principles of the present invention.

FIG. 14 shows card 1400 that may include magnetic emulation circuit 1420. Magnetic emulation circuit 1420 may be included on a short side of a rectangle-shaped card—yet may transmit serially all of the information on a track of financial payment data (e.g., credit and/or debit data). Such transmitted financial payment data may be utilized to validate a financial payment (e.g., a credit card purchase). Any number of magnetic emulation circuits may be included on any side of card 1400. For example, a magnetic emulation circuit may be provided on a long side of a rectangle-shaped card and another magnetic emulation circuit may be provided on the other long side of a rectangle-shaped card. Each magnetic emulation circuit may be utilized to transmit different data or the same data.

Figure 15:
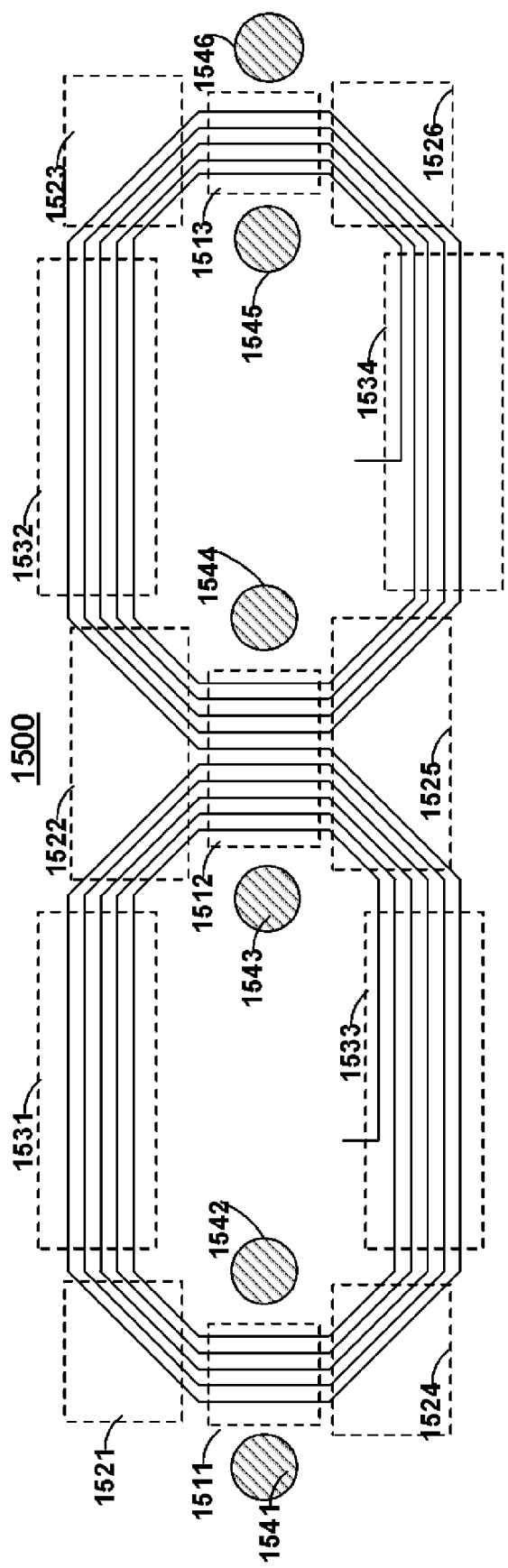
FIG. 15 is an illustration of a circuit constructed in accordance with the principles of the present invention.

FIG. 15 includes circuit 1500 that may include read-head detectors 1541, 1542, 1543, 1544, 1545, and 1546. Circuit 1500 may include a magnetic emulation circuit that includes regions 1511, 1512, 1513, 1521, 1531, 1522, 1532, 1523, 1524, 1533, 1525, 1534, and 1526. Regions 1511-1513 may be operable to communicate with a read-head that passes through regions 1511-1513. The magnetic emulation circuit may include a coil. Regions 1511-1513 may include, for example, coil segments that are parallel to one another. The coil segments may produce an electromagnetic field operable to communicate data to a read-head of a magnetic stripe reader. The coil segments of regions 1521-1526 may be oriented approximately at a 45 degree angle from the coil segments of regions 1511-1513. Accordingly, for example, the orientation offset of regions 1521-1526 from regions 1511-1513 may allow regions 1521-1526 to produce an electromagnetic field that cannot communicate with a read-head of a magnetic stripe reader when regions 1511-1513 are communicating data to a read-head of a magnetic stripe reader. Similarly, the coil segments of regions 1531-1534 may be oriented perpendicular to the coil segments of regions 1511-1513. Accordingly, for example, the orientation offset of regions 1531-1534 from regions 1511-1513 may allow regions 1531-1534 to produce an electromagnetic field that cannot communicate with a read-head of a magnetic stripe reader when regions 1511-1513 are communicating data to a read-head of a magnetic stripe reader.

FIG. 16 shows card layout 1600 that may include flexible PCB layers 1610, 1620, 1630, and 1640 to form card 1650. Layer 1610 may include magnetic emulation circuit 1511. Layer 1620 may include magnetic shielding 1621 and 1622. Layer 1630 may include magnetic emulation circuit 1631. Layer 1640 may include read-head detectors (e.g., read-head detector 1642) and magnetic shielding (e.g., shielding 1641).

Figure 17:
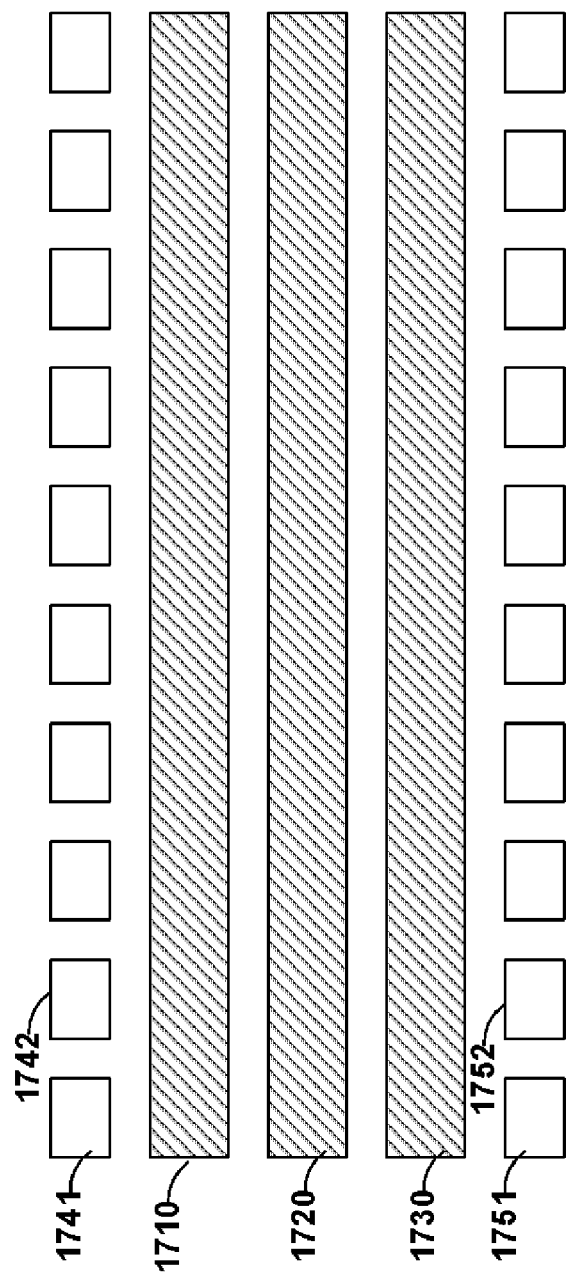
FIG. 17 is an illustration of a circuit constructed in accordance with the principles of the present invention.

FIG. 17 includes circuit 1700 that may include, for example, read-head detectors 1741, 1742, 1751, and 1752. Circuit 1700 may also include, for example, magnetic emulation circuits 1710, 1720, and 1730. Read-head detectors 1741, 1742, 1751, and 1752 may be utilized as read-head detectors and may provide the capability for a read-head to be detected when the read-head is over a particular magnetic emulation circuit or portion of a magnetic emulation circuit. Read-head detectors 1741, 1742, 1751, and 1752 may detect a read-head by sensing, for example, capacitive coupling of a read-head. Alternatively, for example, a read-head contact may be, for example, pressed against another contact when pressure is applied via a read-head.

Persons skilled in the art will appreciate that a display on the card may display a credit card number that does not change with time. Additionally, for example, a magnetic emulator (or multiple magnetic emulators) may magnetically communicate financial data that does not change with time. Such a card may reduce, for example, the effects of physical card theft and card cloning.

One or more light generation devices, such as a Light Emitting Diode (LED), may be provided as part of a card (or other device). Such an LED may produce light, for example, upon a manual input such as a button press, the correct entry of a PIC such as a PIN, and/or the incorrect entry of a PIC. A light emitting device may be operable to produce different colors of light. For example, the incorrect entry of a PIC may produce a red light and the correct entry of a PIC may produce a green light. A PIC may take any form such as a numerical code or a code that include alphabet letters and/or symbols. For example, a PIC may be "A-B-B-B-A" and an "A" button may be provided on a card in addition to a "B" button (as well as other buttons such as a "C," "D," and/or "E" buttons).

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipts may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICs may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICs before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICs based, for example, on time or the number of previous unlock attempts.

A website may be provided where a user enters in his/her credit card number, pays a fee, and a new card is programmed and sent to the user. The new card may include a display to display a portion of the users credit/debit card number in a static form upon entry of an appropriate PIC. Such a card may also include one or more magnetic emulation circuits to transmit the information to a reader. Such a card may or may not, for example, include a portion of a magnetic stripe. For example, three tracks of magnetic stripe data may be communicated via three different emulation circuits, more than three different emulation circuits, one emulation circuits (e.g., tracks communicated serially to all read-heads), or one or more tracks may be represented by magnetic stripe(s) while one or more other tracks may be represented by a magnetic emulation circuit. A track of data may also be partially represented by a magnetic emulation circuit and partially represented by a magnetic stripe.

Figure 18:
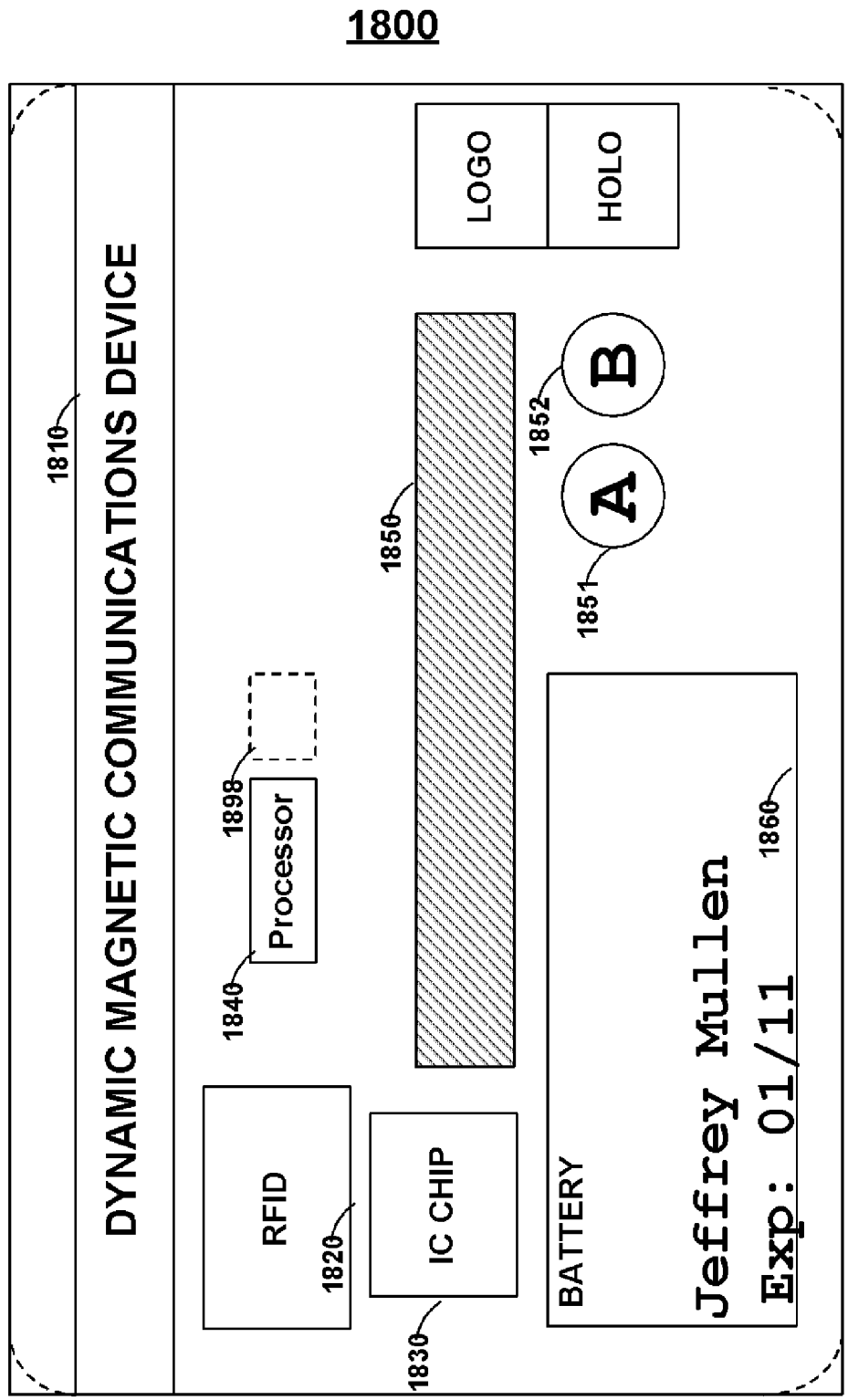
FIG. 18 is an illustration of a card constructed in accordance with the principles of the present invention.

FIG. 18 shows card 1800 that may include, for example, one or more IC chips 1830 (e.g., EMV chips), RFID antennas 1820, processors 1840, displays 1850, dynamic magnetic communications devices 1810 (e.g., magnetic encoders and/or magnetic emulators), batteries 1860, and buttons 1851 and 1852. Additional circuitry 1898 may be provided which may be, for example, one or more oscillators or emulator driving circuits. Persons skilled in the art will appreciate that button 1851 may, for example, be utilized by a user to select one encryption algorithm for a number displayed on display 1850 while button 1852 may be utilized by a user to select a different encryption algorithm. Persons skilled in the art will appreciate that the components of card 1800 may be provided on either surface of a card (e.g., a front or rear surface of the card) or inside of a card. A logo (e.g., of a card issuer) and logo may be provided on either surface of a card.

A button, such as button 1051, may be utilized, for example, to display a number. Such a number may be, for example, encrypted from a secure number based on time or use. For example, one-time use numbers (e.g., a payment number or code) may be retrieved from a list of numbers on memory each time button 1851 is pressed and displayed on display 1850. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a read-head housing may include, for example, multiple read-heads. A read-head detector may, more generally, detect a read-head housing and, in doing so, detect a read-head.

Figure 19:
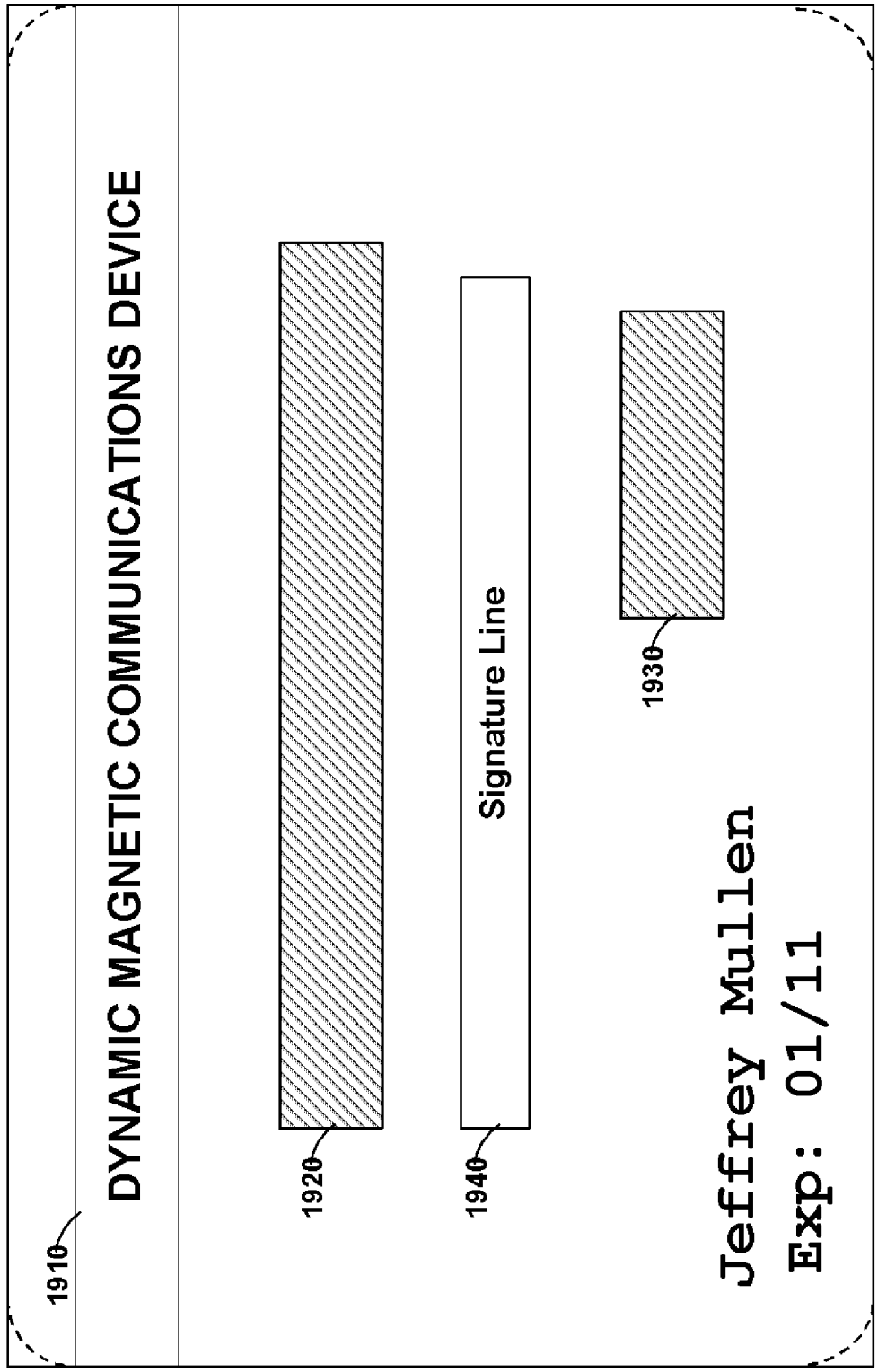
FIG. 19 is an illustration of a card constructed in accordance with the principles of the present invention.

FIG. 19 shows card 1900 that may include, for example, signature area 1940 that may include a material operable to receive marks from a pen (e.g., a signature). Card 1900 may also include, for example, displays 1920 and 1930. Display 1920 may, for example, display a payment number while display 1930 displays a security code (e.g., for online purchase authentication). Display 1920 as well as display 1930 may be utilized on the same side as, for example, dynamic magnetic communications device 1910.

Figure 20:
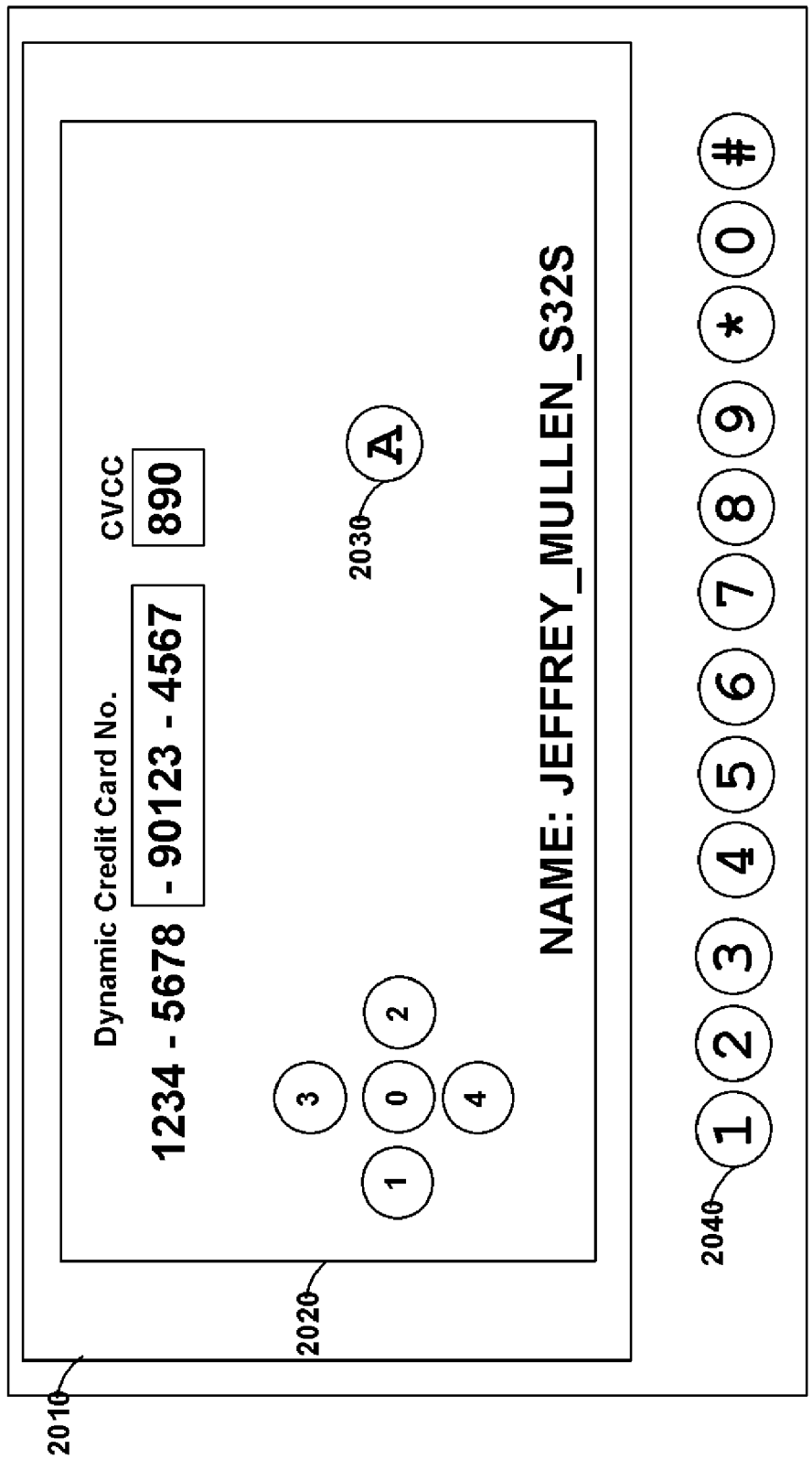
FIG. 20 is an illustration of a personal electronic device constructed in accordance with the principles of the present invention.

FIG. 20 shows personal electronic device 2000 which may be, for example, a portable telephonic device, portable media player, or any type of electronic device. Persons skilled in the art will appreciate that the functionality of a card may be provided on a personal device and displayed through a graphical user interface. Personal electronic device 2000 may include, for example, user inputs 2040 and display 2010. Virtual card 2020 may be displayed on display 2020. Display 2020 may be a touch-sensitive display such that, for example, virtual button 2030 may be provided on virtual card 2020. Persons skilled in the art will appreciate that cards may be provided as virtual cards and a user may interact with such virtual cards in order to provide a variety of functions. Personal electronic device 2000 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:
1. A card comprising:
   an electronic device operable to communicate information to a magnetic stripe reader;
   a first layer of magnetic shielding, wherein said first layer of magnetic shielding is located over said electronic device; and
   a second layer of magnetic shielding, wherein said second layer of magnetic shielding is located over said electronic device, wherein said second layer is located at a point above said first layer,
   wherein said first layer of magnetic shielding includes a first magnetic field limiting material,
   said second layer of magnetic shielding includes a second magnetic field limiting material, and at least one said first magnetic field limiting material said second magnetic field limiting material is a magnetic field blocking material.

2. The card of claim 1, further comprising a battery.

3. The card of claim 1, further comprising a processor.

4. A card comprising:
an electronic device operable to communicate information to a magnetic stripe reader;
a first layer of magnetic shielding, wherein said first layer of magnetic shielding is located over said electronic device; and
a second layer of magnetic shielding, wherein said second layer of magnetic shielding is located over said electronic device, wherein said second layer is located at a point above said first layer,
wherein said first layer of magnetic shielding includes a first magnetic field limiting material,
said second layer of magnetic shielding includes a second magnetic field limiting material, and
at least one of said first magnetic field limiting material and said second magnetic field limiting material is a magnetic material.

5. A card comprising:
an electronic device operable to communicate information to a magnetic stripe reader;
a first layer of magnetic shielding, wherein said first layer of magnetic shielding is located over said electronic device; and
a second layer of magnetic shielding, wherein said second layer of magnetic shielding is located over said electronic device, wherein said second layer is located at a point above said first layer,
wherein said first layer of magnetic shielding includes a first magnetic field limiting material,
said second layer of magnetic shielding includes a second magnetic field limiting material,
said electronic device is a magnetic emulation circuit, and
said first layer of magnetic shielding and said second layer of magnetic shielding are configured to limit a portion of a magnetic field generated by said magnetic emulation circuit.

6. The card of claim 5, further comprising a plurality of displays.

7. The card of claim 5, further comprising:
a radio frequency identification (RFID) antenna; and
an integrated circuit chip (IC Chip).

8. A card comprising:
an electronic device operable to communicate information to a magnetic stripe reader;
a first layer of magnetic shielding, wherein said first layer of magnetic shielding is located over said electronic device; and
a second layer of magnetic shielding, wherein said second layer of magnetic shielding is located over said electronic device, wherein said second layer is located at a point above said first layer,
wherein said electronic device is an emulator,
at least one of said first layer of magnetic shielding and said second layer of magnetic shielding is configured to limit a magnetic field generated by said emulator in a first region of said card,
said first layer of magnetic shielding and said second layer of magnetic shielding are configured to pass said magnetic field in a second region of said card, and a magnitude of the magnetic field external to said card adjacent to said second region is greater than a magnitude of said magnetic field external to said card adjacent to said first region.

9. A card comprising:
an electronic device operable to communicate information to a magnetic stripe reader;
a first layer of magnetic shielding, wherein said first layer of magnetic shielding is located over said electronic device; and
a second layer of magnetic shielding, wherein said second layer of magnetic shielding is located over said electronic device, wherein said second layer is located at a point above said first layer,
wherein said first layer of magnetic shielding includes a first magnetic field limiting material,
said second layer of magnetic shielding includes a second magnetic field limiting material,
said electronic device extends through a first region of said card and a second region of said card,
at least one of said first magnetic field limiting material and said second magnetic field limiting material is on said electronic device in a direction perpendicular to a surface of said card in said first region, and
said first magnetic field limiting material and said second magnetic field limiting material are not on said electronic device in said direction perpendicular to said surface of said card in said second region.

10. The card of claim 9, further comprising a plurality of displays.

11. The card of claim 9, further comprising:
a radio frequency identification (RFID) antenna; and
an integrated circuit chip (IC Chip).

12. A card comprising:
an electronic device operable to communicate information to a magnetic stripe reader;
a first layer of magnetic shielding, wherein said first layer of magnetic shielding is located over said electronic device; and
a second layer of magnetic shielding, wherein said second layer of magnetic shielding is located over said electronic device, wherein said second layer is located at a point above said first layer,
wherein said first layer of magnetic shielding includes a first magnetic field limiting material,
said second layer of magnetic shielding includes a second magnetic field limiting material,
said electronic device extends through a first region of said card and a second region of said card,
at least one of said first magnetic field limiting material and said second magnetic field limiting material is between said electronic device and a surface of said card in said first region,
said first magnetic field limiting material and said second magnetic field limiting material are not between said electronic device and said surface of said card in the second region,
said electronic device is operable to generate a magnetic field in said first and second regions,
a portion of said magnetic field generated in said second region is detectable by a read-head external to said card, and
a portion of said magnetic field generated in said first region is undetectable by said read-head.

13. A card comprising:
a first electronic device operable to communicate information to a magnetic stripe reader;

a first magnetic field limiting layer;
a second electronic device; and
a second magnetic field limiting layer,
wherein the first magnetic field limiting layer and the second magnetic field limiting layer are on opposite sides of the first electronic device, and
at least one of the first magnetic field limiting layer and the second magnetic field limiting layer separates the first electronic device and the second electronic device.

14. A card comprising:
a first electronic device operable to communicate information to a magnetic stripe reader;
a first magnetic field limiting layer;
a second electronic device; and
a second magnetic field limiting layer,
wherein the first magnetic field limiting layer and the second magnetic field limiting layer are on opposite sides of the first electronic device,
at least one of the first magnetic field limiting layer and the second magnetic field limiting layer is between the first electronic device and the second electronic device,
the first electronic device is operable to communicate with a first read-head,
the second electronic device is operable to communicate with a second read-head, and
the first electronic device is operable to communicate with the first read head while the second electronic device communicates with the second read head.

15. The card of claim 13, further comprising a plurality of displays.

16. The card of claim 13, further comprising:
a radio frequency identification (RFID) antenna; and
an integrated circuit chip (IC Chip).

* * * * *

UNITED STATES PATENT AND TRADEMARK OFFICE
CERTIFICATE OF CORRECTION

PATENT NO.        : 8,286,876 B2                                              Page 1 of 1
APPLICATION NO.   : 13/186507
DATED             : October 16, 2012
INVENTOR(S)       : Jeffrey D. Mullen, David Lambeth and Bruce Cloutier It is certified that error appears in the above-identified patent and that said Letters Patent is hereby corrected as shown below:

Claim 1, Column 19
Line 1, replace "at least one said first magnetic field limiting material said" by --at least one of said first magnetic field limiting material and said--.

Signed and Sealed this
Thirteenth Day of November, 2012

David J. Kappos
*Director of the United States Patent and Trademark Office*